United States Patent [19]
Greenberger

[11] Patent Number: 5,492,129
[45] Date of Patent: Feb. 20, 1996

[54] NOISE-REDUCING STETHOSCOPE

[76] Inventor: Hal Greenberger, 182 Laurelwood Dr., Hopedale, Mass. 01747

[21] Appl. No.: 161,713

[22] Filed: Dec. 3, 1993

[51] Int. Cl.⁶ .................................. A61B 5/02; A61B 7/02
[52] U.S. Cl. .......................................... 128/715; 181/131
[58] Field of Search .................................. 128/715, 773, 128/701, 698; 181/131, 126; 381/67

[56] References Cited

U.S. PATENT DOCUMENTS

| | | | |
|---|---|---|---|
| 2,389,868 | 11/1945 | Olson | 181/131 |
| 4,048,444 | 9/1977 | Giampapa . | |
| 4,071,694 | 1/1978 | Pfeiffer . | |
| 4,170,717 | 10/1979 | Walshe . | |
| 4,299,303 | 11/1981 | Clark | 181/131 |
| 4,438,772 | 3/1984 | Slavin . | |
| 4,598,417 | 7/1986 | Deno . | |
| 4,672,977 | 6/1987 | Kroll . | |
| 4,720,866 | 1/1988 | Elias et al. | 381/67 |
| 4,783,813 | 11/1988 | Kempka . | |
| 4,792,145 | 12/1988 | Eisenberg | 128/773 |
| 4,898,179 | 2/1990 | Sirota | 128/715 X |
| 4,985,925 | 1/1991 | Langberg et al. . | |
| 5,025,787 | 6/1991 | Sutherland et al. | 128/698 X |
| 5,209,237 | 5/1993 | Rosenthal . | |
| 5,309,922 | 5/1994 | Schechter et al. . | |

Primary Examiner—Angela D. Sykes
Assistant Examiner—Samuel Gilbert
Attorney, Agent, or Firm—Brian M. Dingman

[57] ABSTRACT

A noise-reducing stethoscope comprising a body sound sensor for placement on a body to detect internal body sounds and output in response an electrical signal, an ambient noise sensor, proximate the body sound sensor, to detect ambient noise and output in response an electrical signal, and a difference comparator for accepting the electrical signals from both sensors and providing in response a difference signal, in which the difference signal contribution from ambient noise is less than the contribution from ambient noise to the body sound sensor electrical signal to cancel noise artifacts in the body sound sensor electrical signal.

49 Claims, 14 Drawing Sheets

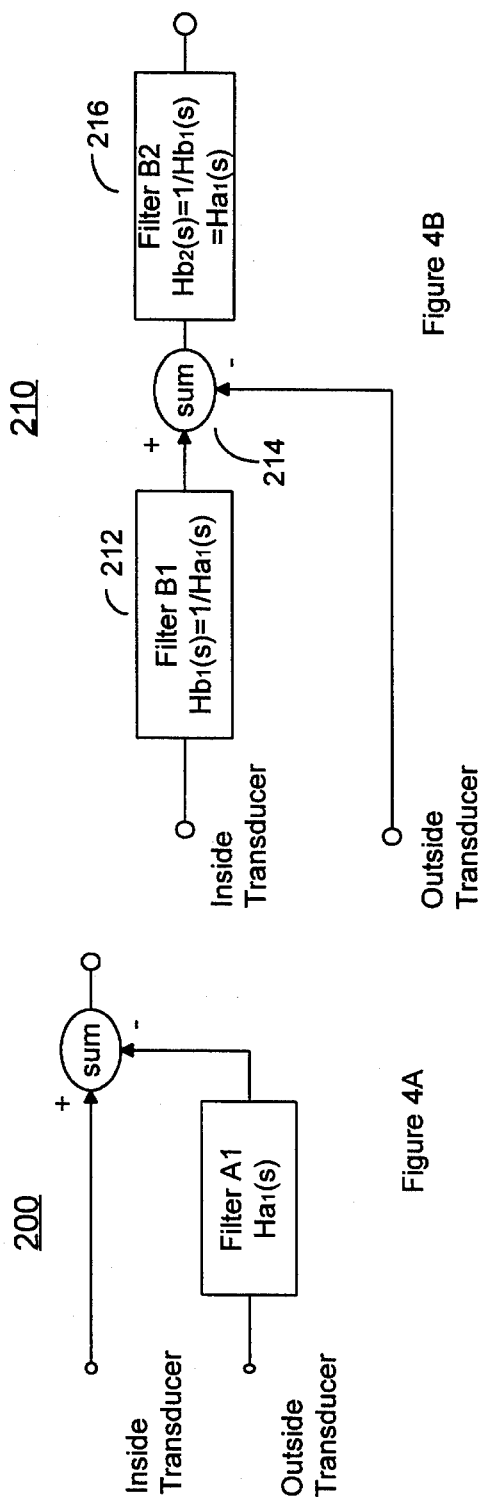
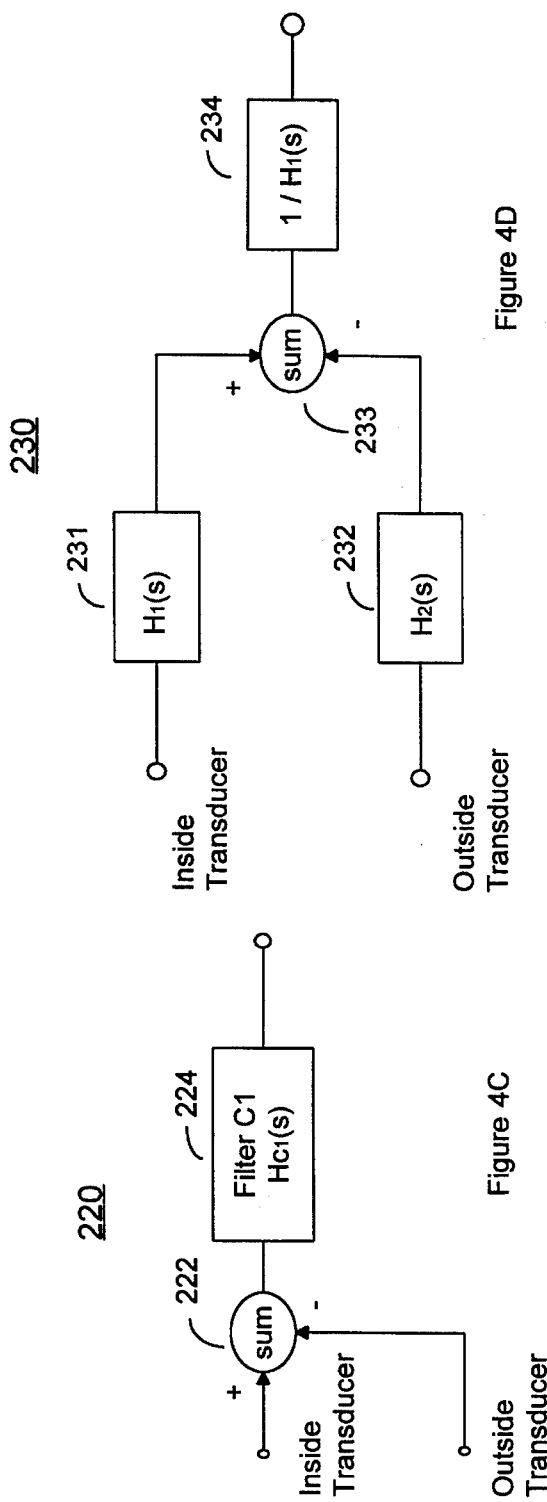

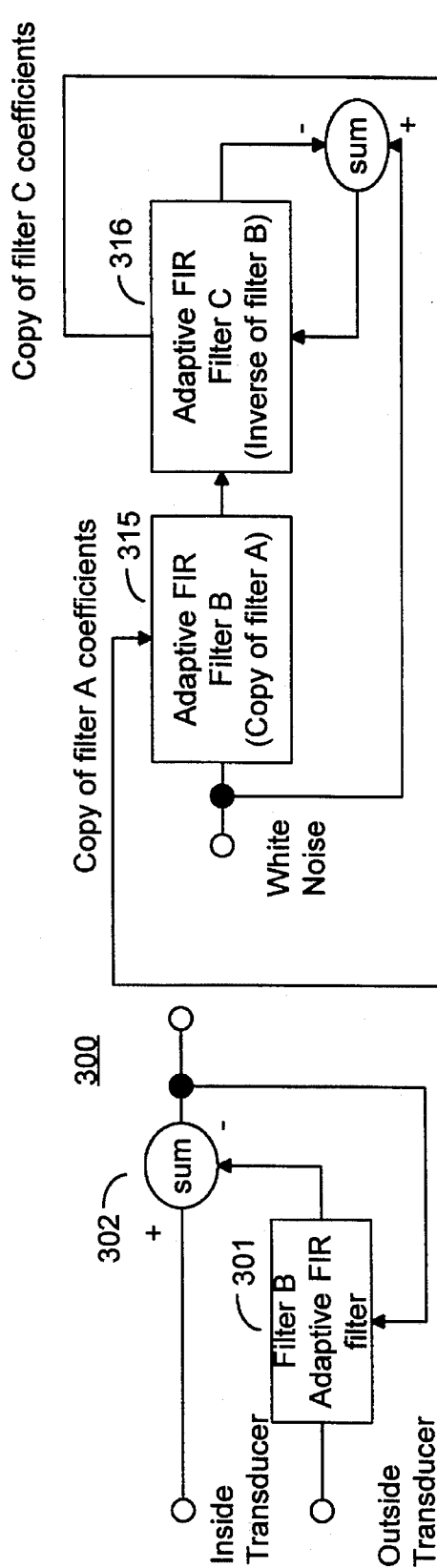
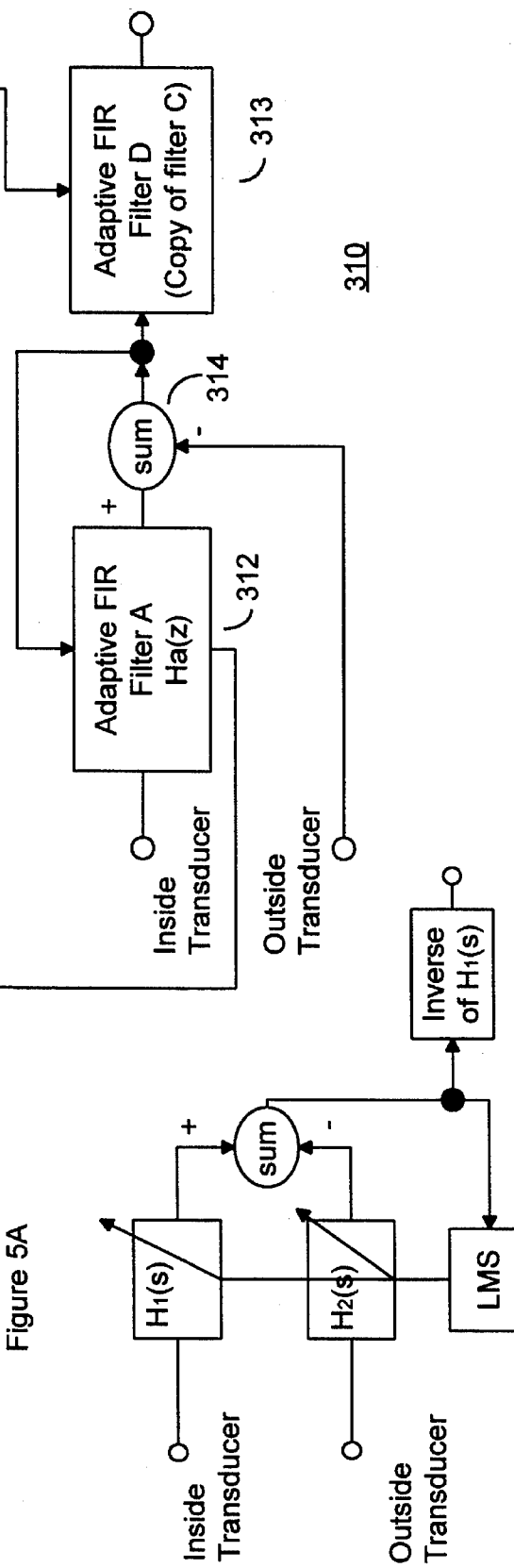
Figure 5A
Figure 5B
Figure 5C

NOISE-REDUCING STETHOSCOPE

FIELD OF INVENTION

This invention relates to a noise-reducing electronic stethoscope.

BACKGROUND OF INVENTION

Stethoscopes are used for listening to internal body sounds such as heart and lung sounds of humans as well as animals. To accomplish a proper diagnosis, the user must be able to hear low volume sounds and subtle sound patterns. In many instances, however, this may be difficult or impossible to achieve due to masking of the signal by ambient noise. Examples of situations in which proper use of traditional stethoscopes is difficult run the gambit from a noisy office or examining room to extreme environments such as in an ambulance or a medical evacuation helicopter.

There have been numerous attempts to increase the stethoscope signal level to overcome the problem with noise. Many of these proposed solutions are electronic stethoscopes which use a microphone element or another type of transducer to convert body vibrations into an electrical signal. The transducer is typically either placed in the bell of the chest piece that is placed on the body, or is fitted into a small section of tubing connected to the chest piece. The signal from the microphone is then amplified and either sent to a small loudspeaker which is connected through tubing to a traditional stethoscope earpiece, or used to drive a conventional set of headphones.

The object of the amplification is to increase the signal level presented to the ears of the stethoscope user. However, these devices are of limited usefulness in high noise environments because the transducer used to transduce the heart and respiration sounds also picks up and amplifies ambient noise. The available signal to noise ratio is determined by the configuration of the chest piece along with the ambient noise level, and no amount of amplification can increase the ratio. Any attempt to amplify desired sounds also amplifies noise. In addition, the earpieces and headsets used with these devices do not sufficiently attenuate ambient noise at the ear. Even if no noise was picked up by the chest piece transducer, noise that leaks through the ear pieces of headsets would mask the desired signals. The signal, in order to be perceived, needs to be amplified until it is louder than the leakage noise by at least 10 dB. Noise leakage through the headset limits the maximum noise level environment in which devices can be used. Only so much amplification can be used to increase the signal above the noise level before the risk of hearing damage becomes significant.

SUMMARY OF INVENTION

It is therefore an object of this invention to provide a noise-reducing stethoscope.

It is a further object of this invention to provide such a stethoscope that increases the interior body sound signal to noise ratio at the user's ears.

It is a further object of this invention to provide such a stethoscope that can be used to listen to cardiac sounds, respiration, or other interior body sounds singly or in combination.

It is a further object of this invention to provide such a stethoscope which at least partially cancels the portion of the signal from the body sound sensor attributed to ambient noise.

It is a further object of this invention to provide such a stethoscope which at least partially cancels ambient noise at the user's ears.

It is a further object of this invention to provide an amplified stethoscope that maintains a constant perceived spectrum of inner body sounds, regardless of the level at which they are played back.

It is a further object of this invention to provide an amplified stethoscope where electrical circuit distortion due to overload conditions is eliminated.

It is a further object of this invention to provide means for the operator to record and play back sounds, where the record function can operate in a pre-trigger mode to allow capture of sounds that occur before the record function is activated, without using an external recording device.

This invention results from the realization that a noise-reducing stethoscope which increases the signal to noise ratio of the signal from the body sound sensor may be accomplished by employing a second noise-sensing transducer near the body sound sensing transducer which detects only ambient noise, filtering the electrical signal output of the ambient noise sensor so that the output of the noise sensing transducer due to an ambient noise source is the same as the output of the body sound sensor due to that same ambient noise source, and subtracting the filtered noise sensor signal from the body sound sensor signal to cancel the contribution from ambient noise to the body sound sensor signal.

This invention also results from the realization that a noise reducing stethoscope which increases the signal to noise ratio at the user's ears may be accomplished using the chest piece cancellation described above, along with a headphone system that attenuates ambient noise at the user's ears. The attenuation can use passive means, active means, or a combination of both. Passive attenuation can be accomplished by use of a sealed ear cup or by blocking the ear canal. Active attenuation can be accomplished by using a headset that includes a noise sensing microphone (either inside or outside the ear cup), a means for filtering and inverting the polarity of the noise signal picked up by the microphone, and amplification and playback means so that the ambient noise signal at the ears is at least partially cancelled by the processed signal from the noise microphone. The filtering can be fixed, adaptive, or a combination of both connected in either an open or closed loop configuration.

The maximum performance of this invention requires the use of chest piece noise cancellation in combination with noise cancellation in the headset. If an active cancellation headset were used along with a standard amplified stethoscope chest piece where the headset was capable of 100% noise attenuation at the user's ears, the system will still be limited by noise that leaks through the chest piece. At a certain ambient noise level (approximately 75 dbSPL C weighted) the noise leakage would mask the desired signal completely. If a chest piece design with perfect noise cancellation were used with a conventional headset, the system will be limited by the noise leakage through the headphones. The system will be limited by the maximum level at which the headset can play (and which the user can stand) and the need to maintain at least a 10 dB signal to noise ratio to be able to perceive the signal. Note that a 10 dB S/N just allows the user to detect the presence of a signal, not discern fine details of the signal. Using a cancellation chest piece or active cancellation headset alone will provide an improvement over the current state of the art in amplified stethoscopes. However, the synergy of using a cancellation chest piece with a cancellation headset provides a performance level considerably greater than what can be achieved with either technology alone.

This invention also results from the realization that a noise reducing stethoscope which maintains a constant perceived spectrum regardless of listening level can be accomplished by including circuitry whose frequency response varies as a function of level in the inverse manner to which human hearing frequency sensitivity varies as a function of level.

This invention also results from the realization that a sufficiently large input signal can overload a fixed gain amplifier. The clipping distortion that would result can be eliminated by the inclusion of limiting circuitry which has a variable gain amplifier where the gain is signal dependent. The amplifier gain is reduced to avoid overload when an input signal would otherwise be large enough to cause the output to clip. Compression of signal dynamic range is used to maximize the perceived signal volume.

This invention features a noise-reducing stethoscope that in one embodiment includes a first transducer for coupling to a body to detect internal body sounds, and a second transducer near the first for sensing ambient noise. The signal from the ambient noise sensor is subtracted from that of the body sound sensor to cancel at least part of the signal due to environmental noise. Noise reducing or attenuating headsets may be used to play the signal back in the user's ears. Another embodiment includes a sound sensing means for coupling to a body to detect internal body sounds, and active noise reduction user earphones for playing that signal. Yet another embodiment includes transducer means for sensing sounds from a body and for sensing ambient noise and producing in response a signal having decreased contribution from ambient noise, and a headset for playing the signal to a user.

BRIEF DESCRIPTION OF THE DRAWINGS

Other objects, features and advantages will occur to those skilled in the an from the following description of preferred embodiments and the accompanying drawings, in which:

FIGS. 4A, 4B, 4C and 4D are four embodiments showing different topologies for using a fixed filter to improve noise cancellation for the stethoscope of this invention;

FIGS. 5A, 5B and 5C are three embodiments of digital adaptive noise filters for the stethoscope of this invention;

The essential problem the stethoscope of this invention addresses is that all known methods for sensing interior body sounds used in stethoscopes today can be contaminated by external noise sources. External electrical noise sources are easily dealt with by using proper circuit design techniques that reduce electrical system susceptibility to external electromagnetic interference and pose no problem for passive acoustical type stethoscopes. What has been more difficult to deal with effectively has been signal contamination due to acoustical noise sources.

The acoustical noise contaminates the desired signal through an additive process. The output of the body sound transducer is the vector sum of the output due to the desired body sounds and output due to the undesired ambient noise. Because this is an additive process, it should be possible to remove the noise contamination by an inverse (subtractive) process. In order to accomplish this, a signal that is an exact replica of the noise component contained in the body sound signal is required. If this signal is available, then it can be subtracted from the body sound sensor signal. This subtraction would then leave the uncontaminated interior body sound signal. There are numerous embodiments discussed in this disclosure that are designed to achieve this subtraction.

There is a two transducer embodiment where the second transducer is located in free space, close to the body sound transducer. This second transducer generates a replica of the noise component of the body sound transducer (although not an exact replica). The output of this second transducer is subtracted from the output of the body sound transducer signal to cancel the noise component of the body sound sensor signal. The degree of cancellation depends on how exact a replica the second transducer signal is to the noise component of the body sound sensor. There are numerous ways in which this subtraction can be accomplished. One way would be to have both transducers connected to a single amplifier where they are wired, either in series or in parallel, with reversed polarity connections. Another method would be to amplify each signal separately, invert the polarity of one of the signals and then sum them together. Other methods would be apparent to those skilled in the art.

Other embodiments apply filtering to the noise signal to try to make it more closely match the noise component of the body sound transducer signal. This filtering can be electrical, mechanical, acoustical, or a combination of any or all of the three. The filtering can also be time invariant or time variant.

Another embodiment performs the required subtraction directly in the transducer by virtue of how the transducer is mounted in the stethoscope chest piece. Acoustical and mechanical elements can also be used here to improve cancellation.

Figure 1A:
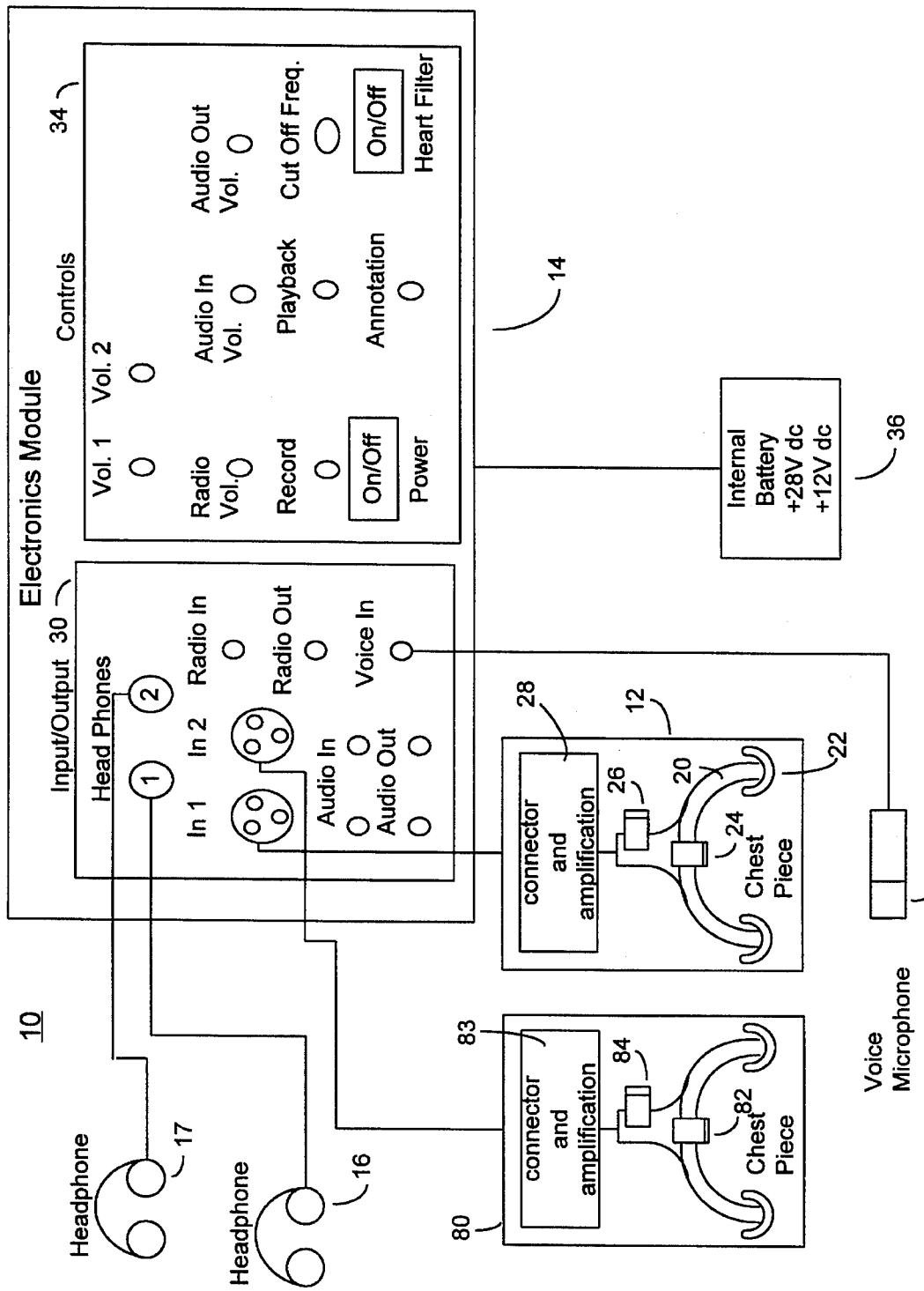
FIG. 1A is a block diagram of a noise reducing stethoscope of the invention.

There is shown in FIG. 1A one embodiment of noise-reducing stethoscope 10 according to this invention. Stethoscope 10 includes three basic sections: chest pieces 12 and 80 for placement on the patient, electronics module 14 for processing the sound signal from chest pieces 12 and 80, and headphones 16 and 17 for providing a sound signal to two users' ears. Headphones 16 and 17 may provide a high head clamping force between the ear cups and the head, as is known in the art, to decrease noise transmission. Headphones 16 and 17 may provide a high head clamping force between the ear cups and the head, as is known in the art, to decrease noise transmission.

Chest piece 12 is shown in FIG. 1A as having a bell-type chest piece 20 with body seal 22. This is for convenience only. The transducers described elsewhere in this disclosure can be mounted to and used with any and all existing acoustic chest piece types. Body sound sensor transducer microphone 24 is mounted inside of bell 20 and is preferably structurally isolated from the bell housing to reduce the amount of noise picked up that is transmitted through the bell housing. Transducer 24 picks up the body sound signal as well as any ambient noise that has leaked through body seal 22. Second, ambient noise sensing transducer microphone 26 is mounted on or near the chest piece in close proximity to transducer 24, but outside of housing 20. Transducer 26 is also structurally isolated from housing 20. Outside transducer 26 picks up only ambient noise because the body is a very inefficient sound radiator to free air. The two transducers should be near each other so that the noise picked up by each transducer is highly correlated. Second chest piece 80 is identical to chest piece 12, with internal microphone 82, and external microphone 84.

The two transducers in each chest piece need to be as close to each other as is physically possible for the fixed cancellation filter implementation of the stethoscope. Any displacement of the two devices in space would cause there to be a phase difference in the noise that arrives at the two mics that changes as a function of the direction of arrival of the noise source. Any phase difference due to this effect will reduce the maximum noise cancellation that is achievable. The adaptive filter implementation of the stethoscope can compensate for this effect but it will still benefit from the transducers being as close together as possible. The ability of the adaptive system to cancel noise depends on the correlation of the noise in the two transducer outputs. Spacing the microphones apart can reduce the correlation and therefore reduce the maximum cancellation possible.

Chest piece 12 also includes in a preferred embodiment signal amplification and an electrical connector, 28. The amplifier is useful for increasing the level of the signal that is transmitted through the cable that connects the chest piece to electronics module 14. This amplification helps reduce the susceptibility of the system to induced noise from outside electromagnetic interference. To reduce the expense and size of the chest piece, the amplification could be accomplished in the electronics module 14, but at the expense of reduced noise immunity.

The use of a connector allows the user to change chest pieces easily. Different chest pieces may require different filtering characteristics in order to maximize cancellation. The filter electronics could be included in the chest piece housing. This would be the easiest method of ensuring that the correct filtering was used with each chest piece. However, this arrangement would require the chest piece to become physically larger to accommodate the extra circuitry. Another alternative is to include the filter circuits in the electronics module along with some logic circuitry to detect which chest piece is connected. The chest piece type can be sensed and the filter characteristics changed automatically. This could be accomplished by using extra pins in the chest piece connector. The presence or absence of these pins could be sensed by circuitry in the electronics module and logic circuits would then switch in the appropriate filter components. A manual switch, rather than automatic sensing, could also be provided which the user would switch to the correct setting for the chest piece being used. The adaptive systems automatically compensate for different chest piece characteristics and do not need this switching capability.

FIG. 1A does not show any internal detail of electronics module 14, instead simply showing the preferred embodiment of the front face which includes an input/output section 30 with connectors for two chest pieces, audio input and output jacks, a voice input jack, a radio input and output jack, and two headphone outputs. Audio input and output jacks are provided for making and playing back archive recordings. The audio output jacks can also be connected to an external speaker to provide a simultaneous monitoring capability for a group of people. The ability of the chest piece to cancel ambient noise also significantly increases the gain before feedback that it is possible to achieve with the external speaker, thus allowing the system to play at a greater volume, which allows more people to listen in. The voice input, radio in and radio out jacks are provided for connection into a radio communication system. The voice input accommodates a microphone 32 which can also be used for adding voice annotation to the archive recordings. Included in controls section 34 is volume adjustment for each chest piece, the radio, and the audio input and outputs. Also included are an on/off switch and cut off frequency control for the cardiac filter described in more detail below, recording and playback controls for the hardware recording system, voice annotation switch, and a system power switch. The recording and playback controls could also be located on the chest piece for ease of use. The power is provided as shown schematically by block 36 with one or more of an internal battery as well as the ability to accept DC voltages between 9 and 36 VDC for use with an automotive and aircraft power systems. The output is provided to headphones 16 and 17 worn by the users.

Figure 1B:
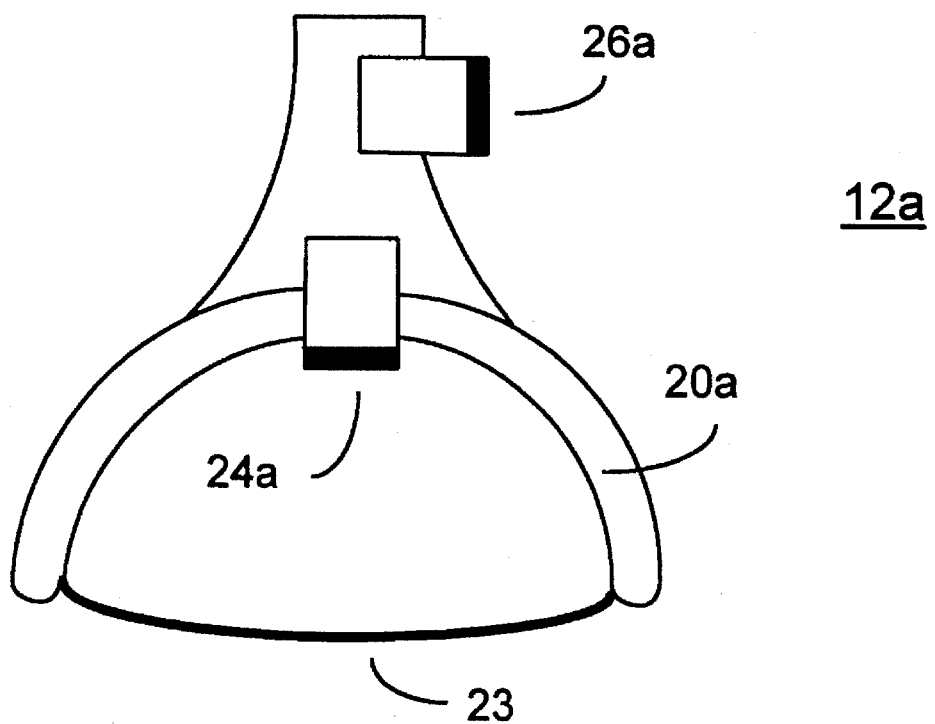
FIG. 1B is a schematic diagram of a diaphragm-type chest piece useful in this invention.

FIG. 1B is a schematic diagram of an alternative chest piece design for the noise reducing stethoscope of this invention. Chest piece 12a includes housing 20a closed by diaphragm 23 which rests against the patient's skin in place of body seal 22, FIG. 1A. Internal microphone 24a and external microphone 26a function as described above.

FIGS. 2A, 2B, 3A and 3B detail two preferred embodiments of the noise reducing stethoscope of this invention. The major differences between the different embodiments revolve around whether the signal processing portion of the invention is accomplished using analog or digital techniques, and whether the cancellation filters used are time invariant (fixed) or time variant (adaptive).

There are four possible embodiments. Analog fixed and adaptive noise cancellation filter embodiments, and digital fixed and adaptive noise cancellation filter embodiments. In each case the difference between the fixed and adaptive embodiments is in the noise cancellation filter. The digital embodiments are essentially the same as the analog embodiments except for the required circuitry to convert the microphone signals from analog to digital form, and the circuitry to convert the headphone signal from digital back to analog form. The extra circuitry includes anti-alias filters 152, 153, 162 and 163, A/D converters 154, 155, 164, 165, reconstruction filters 176, 184, 192, and D/A converters 174, 182 and 190, FIGS. 3A and 3B.

Figure 2A:
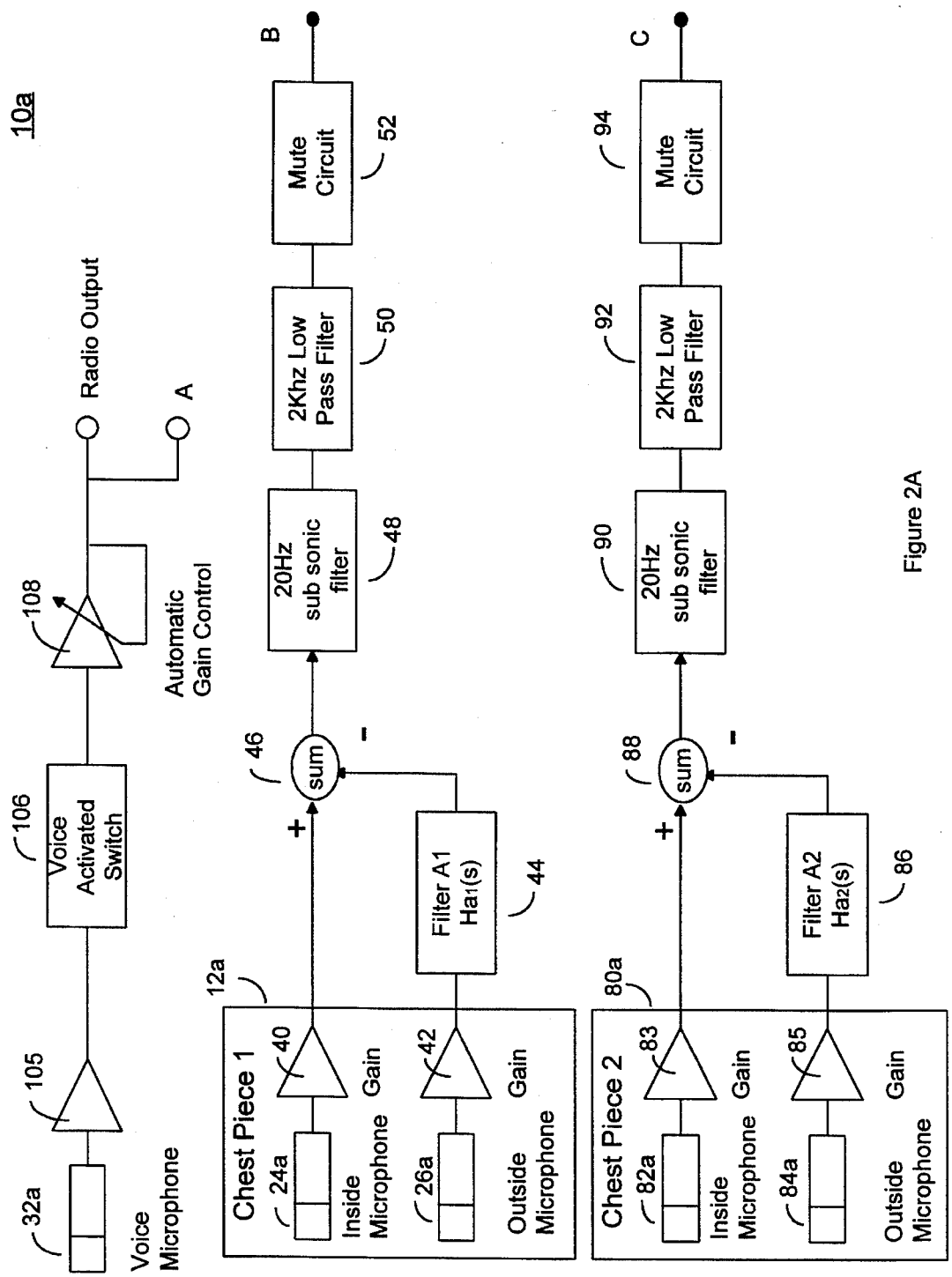
FIGS. 2A and 2B are a schematic block diagram of an analog embodiment of the noise reducing stethoscope of this invention using a fixed cancellation filter.
Figure 2B:
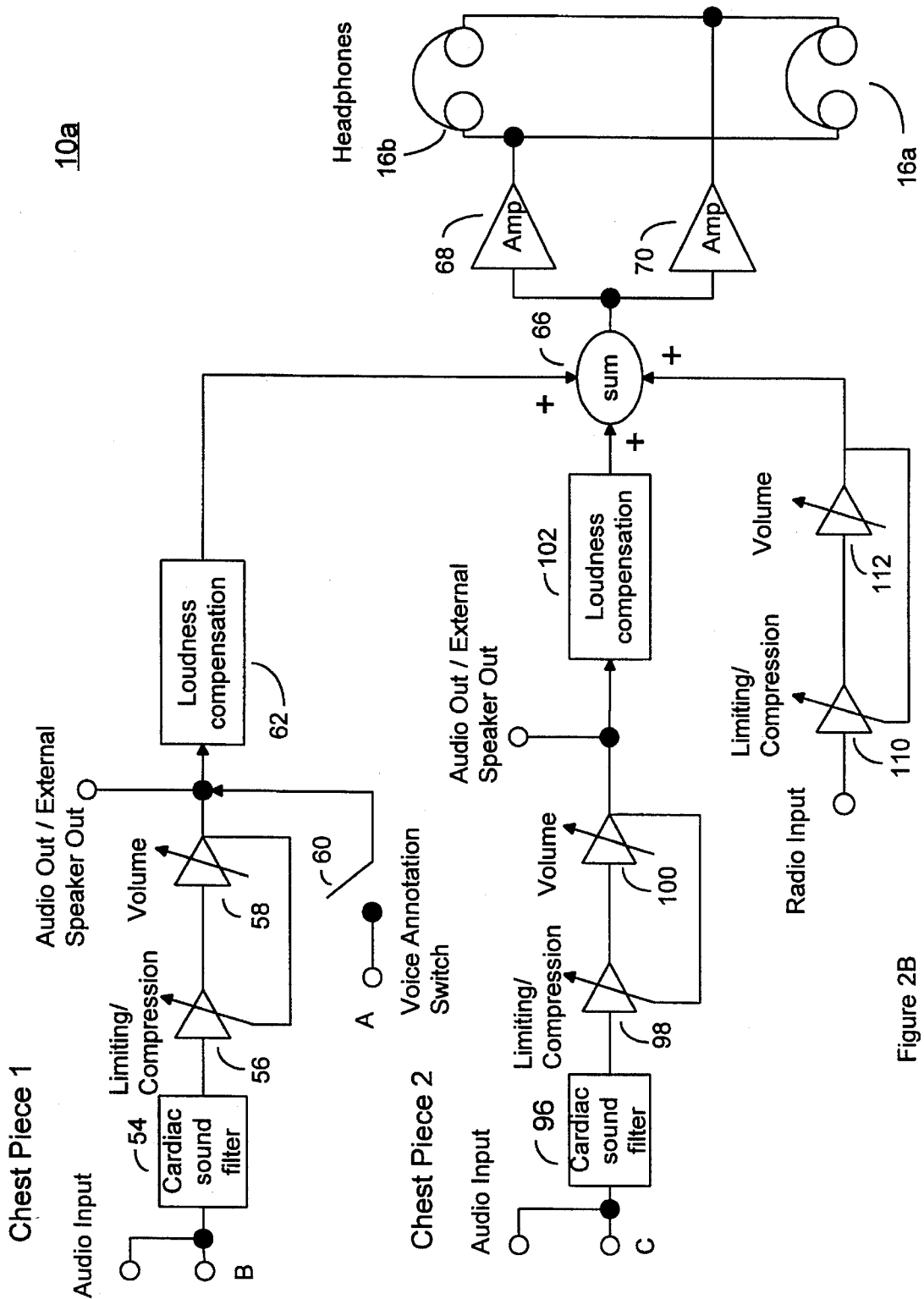
Figure 3A:
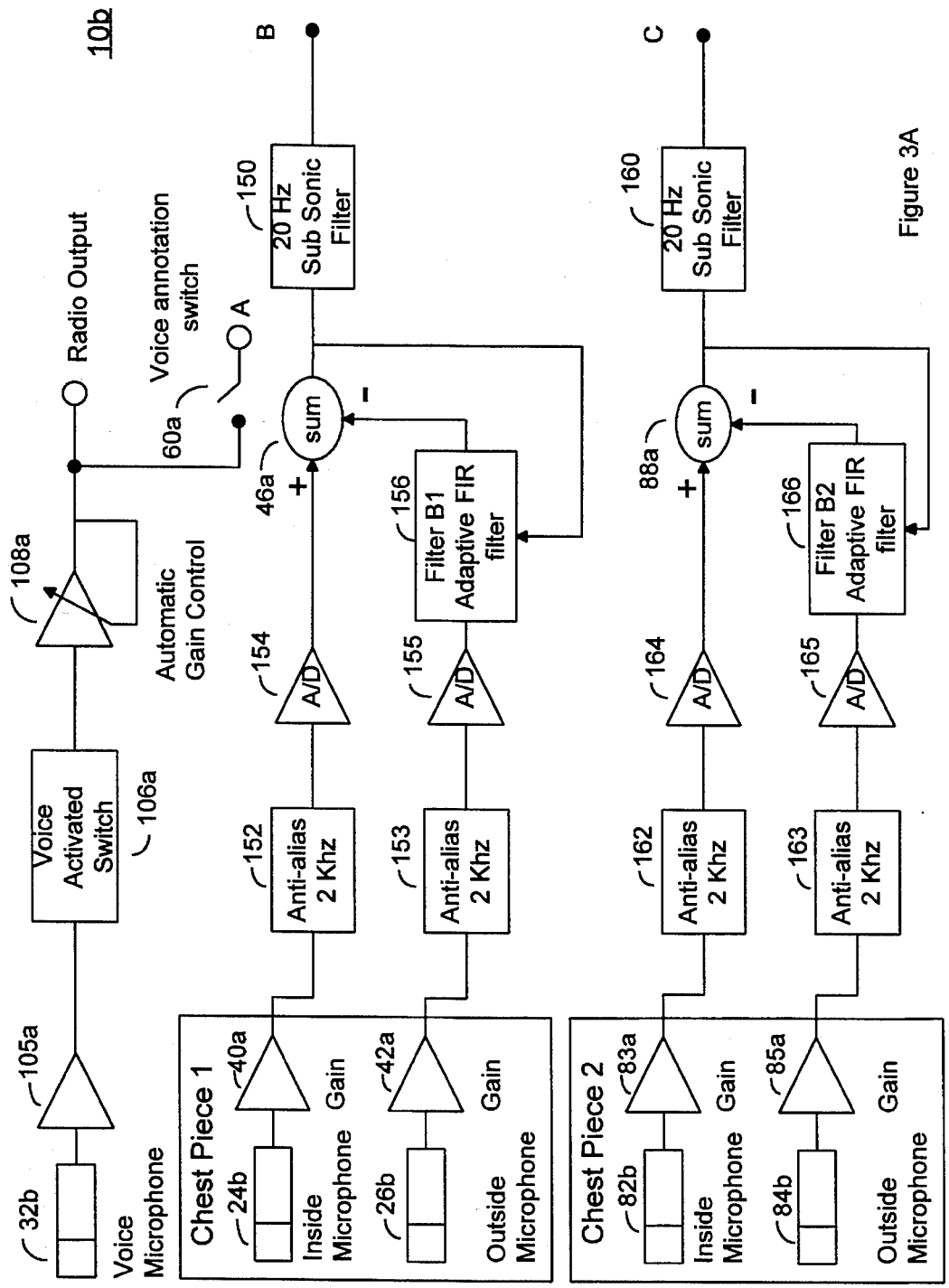
FIGS. 3A and 3B are a similar block diagram for a digital embodiment of the noise reducing stethoscope of this invention using an adaptive cancellation filter.
Figure 3B:
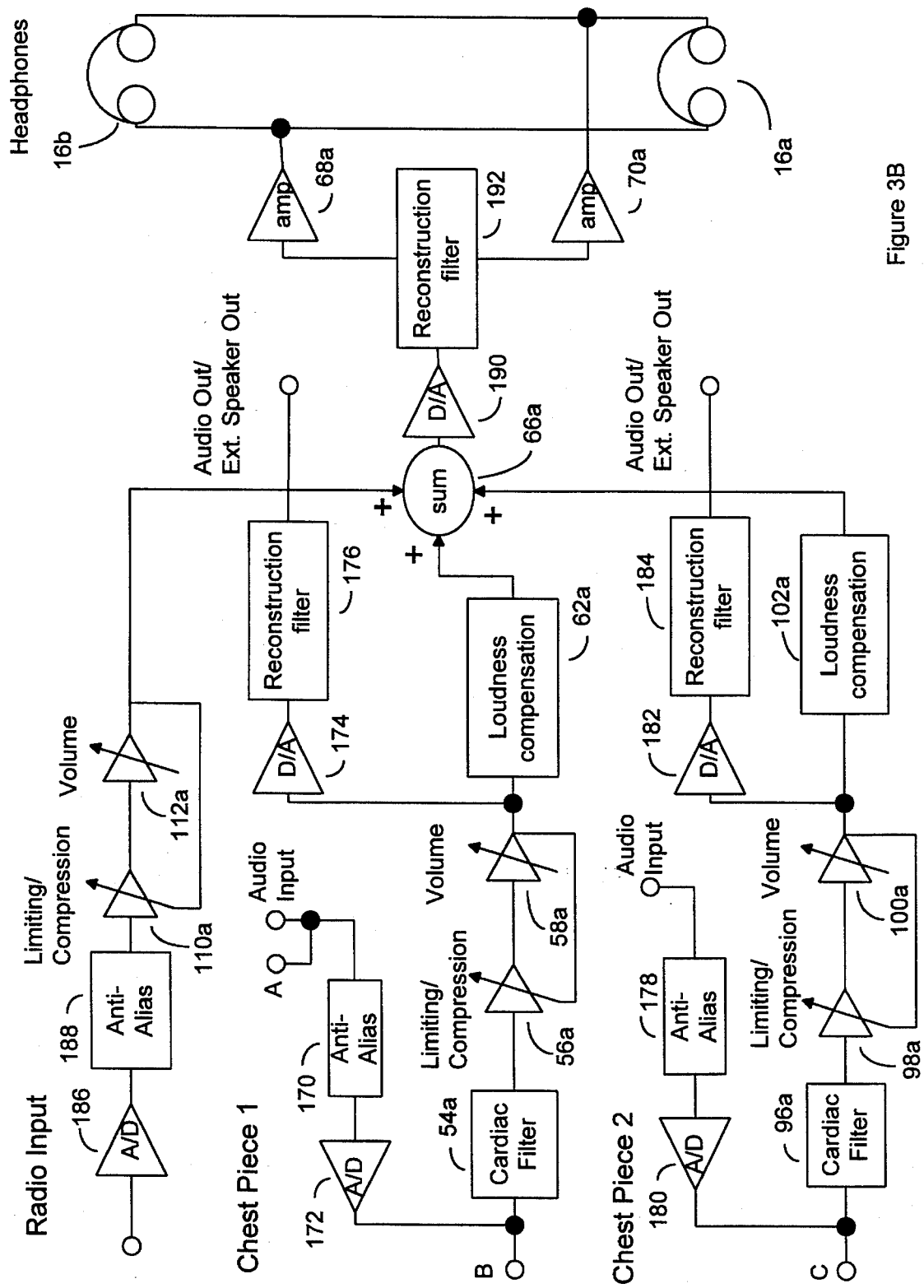

FIGS. 2A and 2B are a schematic block diagram of the analog fixed cancellation filter embodiment, and FIGS. 3A and 3B are a schematic block diagram of the digital adaptive cancellation filter embodiment. The analog adaptive filter embodiment and the digital fixed filter embodiment are not shown.

In FIGS. 2A and 2B, stethoscope 10a can accommodate one or two chest pieces 12a and 80a, simultaneously. Each chest piece includes an inside microphone 24a, 82a, an outside microphone 26a, 84a, and an amplifier 40, 42, 83, 85, for each of the four channels. The output of the chest piece outside transducer is passed through a filter 44, 86 which compensates for the difference between the response of inside transducers 24a, 82a and the response of outside transducers 26a, 84a to an ambient noise source. The filter is preferably placed in series with the output of the outside transducer so the output of that filter due to an ambient noise source is the same as the output of the inside transducer due to the same ambient noise source. The output of the filter is then subtracted from the output of the inside transducer at summer 46, 88 so that the noise contained in the inside transducer signal is fully or at least partially cancelled, while the signal sensed from the body is left unchanged. The frequency response and gain of the filters are adjusted to maximize the amount of cancellation when the chest piece is placed against the skin of the patient.

The signal from summer 46, 88 is then provided to 20 Hz subsonic filter 48, 90, which filters out frequencies below the threshold of human hearing which could not be perceived by the user but would be amplified by the system. This out of band energy could cause the limiting and compression circuitry to activate gain reduction prematurely thus limiting the maximum playback volume of the desired signal. Filters 48, 90 are preferably fourth order or higher high-pass filters set to a cutoff frequency of 20 Hz.

Filters 50, 92 are second order or higher low pass filters with a cut off frequency of 2 KHz. These filters are used to eliminate noise above 2 KHz. There is no significant energy above this frequency in the transduced interior body sounds. In addition, the displacement in space between the inside and outside transducers begins to have a significant effect on the maximum attainable cancellation above 2 KHz. The subtraction performed by summers 46, 88 could actually cause the noise to increase above 2 KHz rather than cancel due to this additional phase shift, so the energy above 2 KHz is removed.

Figures 6A, 6B:
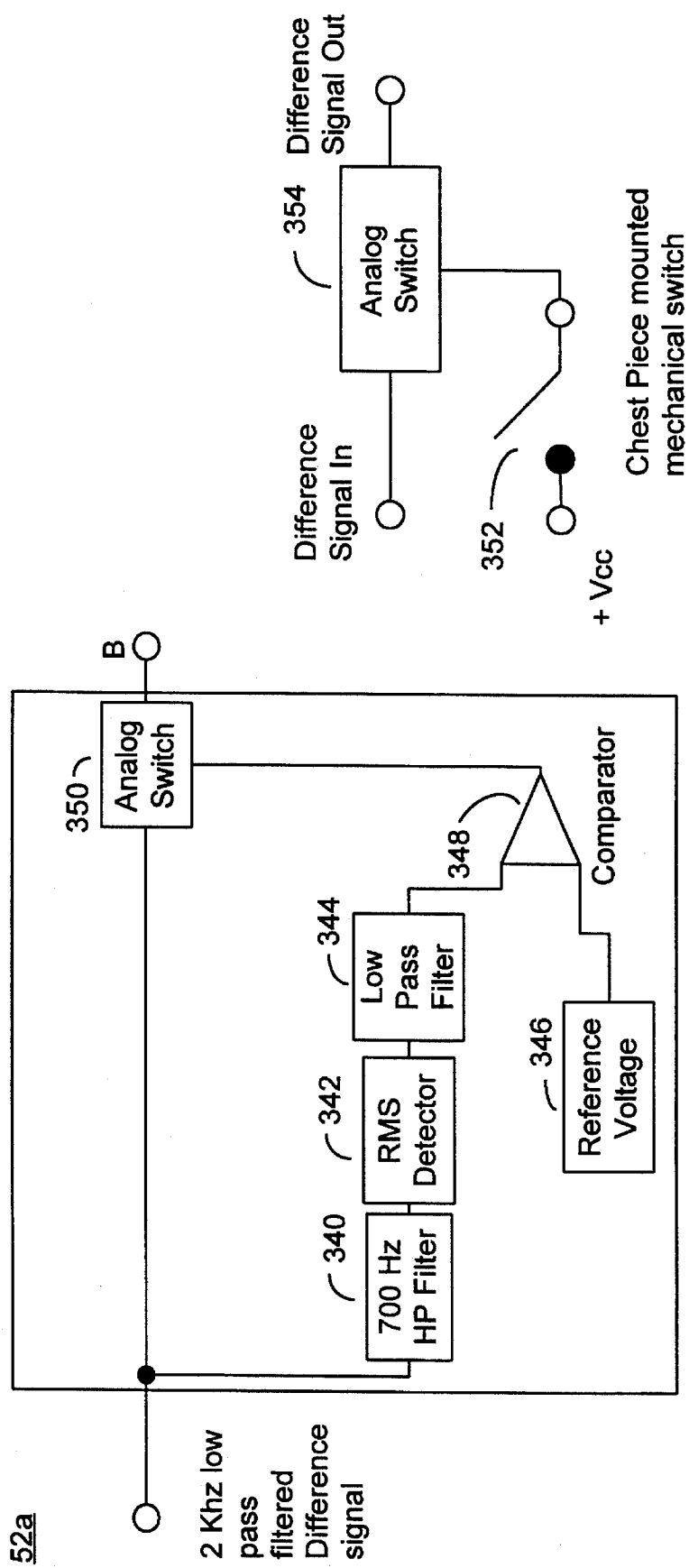
FIGS. 6A and 6B are more detailed block diagrams of two embodiments of the mute circuit of FIGS. 2A and 3A.

Mute circuit 52, 94, shown in more detail below in FIGS. 6A and 6B, is provided to mute the output when the chest piece is lifted from the patient to prevent amplification of the ambient noise.

Voice microphone 32a, amplifier 105, voice activated switch 106, automatic gain control 108, volume control 112, along with radio input and output connections are provided for use with a radio communication system. The voice microphone can also be used in conjunction with manually operated switch 60 to provide voice annotation for archive recordings or for voice communication when the system is used in teaching situations where there may be multiple headphone listeners or when the system is connected to an external speaker system.

Manually switched cardiac sound filter 54 and 96, FIG. 2B, referred to as "heart filter" in FIG. 1A, are designed to filter out cardiac sounds so that respiration can be more easily heard. The spectral energy of cardiac sounds tends to be concentrated in the low frequency region while the spectral energy of respiration sounds tends to be concentrated at mid and high frequencies. A high pass filter can therefore be used effectively to separate the respiration sounds from the cardiac sounds. The filter should be a second order or higher high pass filter. The cutoff frequency should be user variable so that the user can trade off between the level of cardiac sound heard and the amount of low frequency respiration sounds that are filtered out. The cutoff frequency should be adjustable from 20 Hz to 300 Hz for optimum use. The filter can be easily accomplished using a device such as the National Semiconductor AF100 Universal Active Filter integrated circuit or by using standard op amp active filter configurations such as a state variable design. In both of these cases, a second order high pass filter where the cut off frequency is varied by varying one resistor value is easily accomplished. The circuitry is fully described in the National Semiconductor data sheets for the AF100 or in standard active filter texts such as "Introduction to the Theory and Design of Active Filters" by L. P. Huelsman and P. E. Allen.

Figure 7B:
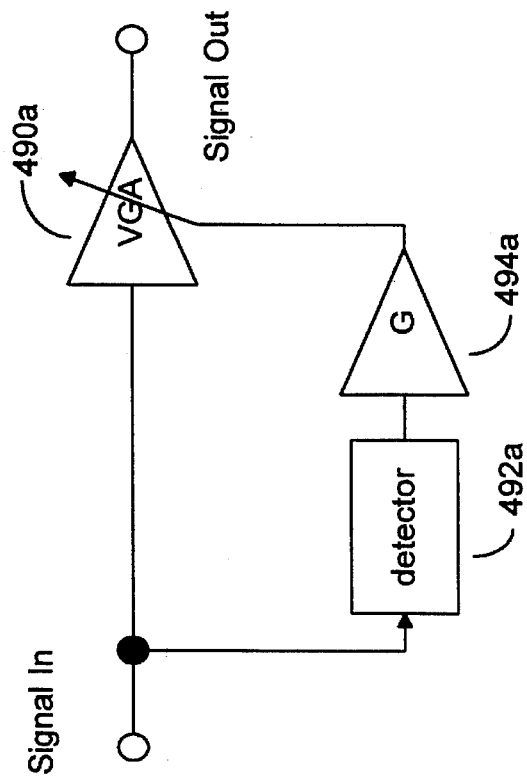
FIGS. 7A and 7B are schematic block diagrams of two embodiments of the compression/limiting circuit for the noise reducing stethoscope of this invention.
Figure 7A:
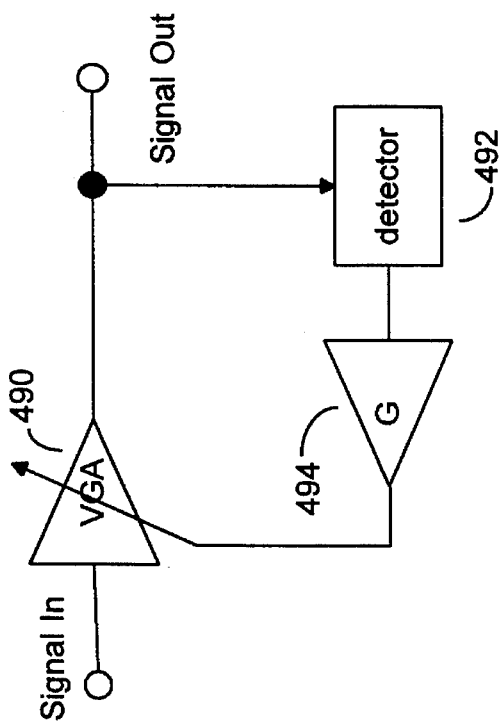

Limiting/compression circuitry 56, 98, 110 modifies the signal dynamic range by adjusting the gain of a variable gain element. FIGS. 7A and 7B show detailed diagrams of limiting/compression circuitry and its operation is described later. The compression ratio of gain varying circuits is defined as the ratio of the change in output level to the change in input level expressed in dB. Limiting typically refers to a compression ratio of 10:1 or greater. This ratio states that for a 10 dB increase in the input signal level, the output signal level will increase by 1 dB. Limiting is used to avoid overdriving the electronics which can cause sever clipping distortion. Limiting circuits modify the signals dynamic range only after some pre-set threshold has been reached or exceeded.

The same circuitry can be used to perform dynamic range compression as well. Compression typically refers to gain varying circuits with compression ratios of less than 10:1. Compression circuits tend to be active over the entire dynamic range of the signal, not just above a set threshold as is the case with limiting circuits. Compression allows the average level of the signal to be amplified more than would otherwise be possible before overload distortion occurs. Compression can therefore be used to increase the perceived volume of a signal. Using compression in conjunction with limiting allows the perceived volume of a signal to be increased while eliminating the occurrence of overload distortion. Note that the compression and limiting circuits are shown for the interior body sounds as well as the radio signals. Radio communication will benefit from this type of processing as well.

Volume controls 58 and 100 adjust the playback volume.

Loudness compensation circuits 62 and 102 provide the user a constant perceived interior body sound spectrum, regardless of the playback level. The circuitry is designed to maintain the same perceived spectrum as that of a set reference. In this case, the reference is determined to be the spectrum and level of a standard acoustic stethoscope operated in a quiet environment.

The circuitry compensates for a phenomenon of human hearing where the sensitivity of the ear to low frequencies relative to mid frequencies varies depending on the listening level. The ear is more sensitive to low frequencies at high listening levels than it is at low listening levels. With an amplified stethoscope such as disclosed herein, as the amplification is increased, the perceived level of low frequency information would increase. The loudness compensation circuitry compensates for this effect. The spectrum of the signal is modified as a function of volume in such a way as to maintain a constant perceived spectrum regardless of level. When the listening level is above the reference level, the low frequency content will be reduced accordingly. When playback is below the reference level, the low frequency content will be increased. The compensation is based on the work of S. S. Stevens, "Perceived Level of Noise by Mark VII and Decibels (E)", Journal of the Acoustical Society of America, Vol. 51, pages 575–601 (1972) and that of Tomlinson Holman and Frank Kampmann, "Loudness Compensation: Use and Abuse", Journal of the Audio Engineering Society July/August 1978, Vol. 26, number 7/8. There are many known implementations of appropriate loudness compensation circuits in music reproduction systems which can be adapted for use in this invention, some of which are described in the above references.

The chest piece signal or signals and any signal received over the radio are then provided to summer 66. The chest piece signal or signals could also be provided to the system radio output. The signal from summer 66 is provided to amplifiers 68 and 70 for the left and right speakers of headphones 16a and 16b.

All of the function blocks identified in FIGS. 2A and 2B may also be included in the digital embodiments. The blocks for filtering, summation, muting, volume control, dynamic range processing, and dynamic equalization (loudness compensation) in the digital system are accomplished by combining together different software sub-routines and running them on a digital signal processing chip. Limiting is accomplished by using a multiply operation where the value of the multiplier is signal level dependent. It will have the value of one for signal levels less than a set threshold, and some value less than one for values that exceed the threshold. Compression is accomplished in a similar manner except that the threshold will be changed or eliminated and the value of the multiplier as a function of signal level will be different. Loudness compensation can also be easily accomplished by using either an FIR or IIR filter and adjusting the filter coefficients in an appropriate manner as a function of the average signal level. All of the basic sub-routines use exiting processing techniques. Most of the code segments are available from the DSP chip manufacturers directly and can be configured to run together with minimal programming effort. The major benefit of the digital system is its ability to use a more complex cancellation filter to perform a better transfer function match than what can be done in the analog system given the space and power constraints that the need for portability imposes.

FIGS. 3A and 3B are together a schematic block diagram of a digital adaptive cancellation filter embodiment of the noise reducing stethoscope of this invention. This is the preferred embodiment of the digital system. This system is essentially identical to the digital fixed cancellation filter embodiment, except for the substitution of an adaptive FIR cancellation filter for a fixed cancellation filter, and the elimination of the mute function, as the adaptive filter eliminates the requirement. In the adaptive case, the output of the summer 46a, 88a is fed back to the control input of the adaptive filter. This data is used by the adaptation algorithm to modify the filter tap coefficients. The coefficients are modified by the algorithm in such a way as to make the output of the filter as similar to the inside transducer signal as possible. This will in turn maximize the noise cancellation of the system with the topology shown. The prototype system used an FIR filter length of 256 taps with a 6 KHz sample rate. The well known LMS algorithm was used to adapt the filter coefficients. It should be understood that there are many other algorithms which could be used in place of the LMS algorithm to adapt the filter coefficients to provide noise cancellation such as RLS, FRLS, block LMS, etc. It should also be understood that there are other types of filter structures, such as IIR, and other length FIR filters which can also be used in an adaptive configuration. All of these possible configurations employ the basic concept of using a filter of some type whose frequency response can be varied dynamically, connected in a topology designed to cancel noise in a desired signal, along with some algorithm or control signal that adjusts the frequency response of the filter in such a way as to maximize the noise cancellation in the desired signal. The use of adaptive filters in noise cancelling applications is fully described in "Adaptive Signal Processing", by Bernard Widrow and Samuel D. Stearns.

For an analog adaptive filter embodiment of the noise reducing stethoscope of this invention, the operation is identical to that described for FIGS. 2A and 2B with the following changes. The fixed filter has now become adaptive. The type of filter used can be varied depending on the degree of complexity one wishes. A simple system would use a second order low pass filter such as the one used in the fixed filter implementation case where the cut off frequency and gain can be varied by a control signal. The gain can be adjusted by looking at the energy in the spectrum of the output of the summer at approximately 300 Hz and a control signal is generated to vary the gain to minimize the energy in this band. A similar control voltage can be generated to vary the cut off frequency to maximize noise cancellation by looking at the spectrum at higher frequencies. A more complicated system could use multiple band filters where a control voltage was generated to control the level of each band. This is analogous to what the digital adaptive filter accomplishes. Also, the mute circuit can be eliminated. The adaptive ability of the filter removes the need for a mute circuit. It will constantly adapt its frequency response to maximize cancellation, regardless of the position or orientation of the chest piece. The major benefit of the adaptive digital system over this adaptive analog system is its ability to use a more complex cancellation filter to perform a better transfer function match than the analog system can accomplish given the space and power constraints that the need for portability imposes.

Although not shown, it is possible to have a system that is a mix of analog and digital functions where, for example, adaptive filtering is performed digitally and other signal processing functions are accomplished using analog techniques.

FIGS. 4A through 4D detail a preferred embodiment and three alternative embodiments of topologies for obtaining noise cancellation using fixed cut off frequency filters such as that shown in FIG. 2A. The preferred embodiment, filter 200, FIG. 4A, uses a filter with a low pass response. The exact response of the filter will depend on the exact configuration of the chest piece, including its internal volume, the opening surface area, the presence of a diaphragm, and how well the two transducer responses and their amplifier gains are matched. A prototype system uses a second-order low pass filter with the corner frequency at 700 Hz and a Q of 1. The gain is unity at DC. The filter transfer function $Ha_1(s)$ was generated by placing the chest piece against a surface which simulates the chest wall. An external pink noise source feeding a high quality loudspeaker was used to generate broad band ambient noise. The output spectrums of the inside and outside microphones were then measured. $Ha_1(s)$ is calculated by dividing the spectrum of the output of the inside transducer by the spectrum of the output of the outside transducer. When the filter is placed in series with the output of the outside transducer and the output of the filter is subtracted from the output of the inside transducer as shown in FIG. 4A, the ambient noise picked up by the inside transducer will be cancelled.

The first alternative embodiment 210, FIG. 4B, includes a cancellation filter 212 placed in the inside transducer signal path rather than the outside transducer signal path. In this case, the filter response required would be the inverse of the filter response of the preferred embodiment described above. This would give, for the prototype system example, a filter with a complex zero pair at 700 Hz with a Q of 1 and a pair of real poles at infinity (to generate an inverse filter, poles become zeroes and zeroes become poles). In actual use, the poles could be moved to 2 KHz, because there is no usable signal above that frequency and the system has the additional filtering to eliminate noise components above that frequency. The resulting filter would have a high pass shelf characteristic. This embodiment also requires additional filter 216 after summer 214 to correct the response changes which the signal incurred by being passed through the cancellation filter 212. Filter 216 would be the inverse of filter 212. These filters can be realized by using standard active filter synthesis techniques.

A second alternative embodiment, filter 220, FIG. 4C, does not use a cancellation filter at all. The output of the outside transducer is directly subtracted from the output the inside transducer at summer 222. Cancellation would occur in the frequency range where the transfer functions from an ambient source to each transducer were the same. Above this frequency, the output of the subtraction could cause an increase in the noise level. A low pass filter could be used to remove this extra noise. This embodiment would have a lower cost than the preferred embodiment but it would have a reduced signal bandwidth as compared with the preferred embodiment. The frequency where the subtraction performed by summer 222 begins to cause an increase in the signal noise level would be lower than it would in either of the implementations that use a cancellation filter. For the prototype case, a filter cut off frequency of approximately 700 Hz would be needed. The system bandwidth would be 700 Hz as opposed to 2 KHz for the embodiments where a cancellation filter is used.

A third alternative embodiment 230, FIG. 4D, is a combination of the described embodiments where some filtering is done in the inside transducer signal path by filter 231 and some filtering is done in the outside transducer signal path by filter 232. In this case, the filtering that is done in the inside transducer signal path would require a compensating inverse filter 234 after the summation 233 to correct the frequency response effects of the first filter on the desired signal.

FIGS. 5A, 5B and 5C detail a preferred and two alternative embodiments of a digital adaptive noise cancellation filter such as shown in FIG. 3A. Preferred filter arrangement 300, FIG. 5A, use a fixed length FIR digital filter 301 placed in the outside transducer signal path where the coefficients are updated using the LMS algorithm. The LMS algorithm squares the output of the summer 302 (which is also known as the error signal) and uses it as an estimate of the gradient of the error signal. This gradient estimate is used to update the coefficients. Knowledge of the gradient of the error with respect to the filter coefficients is useful to determine how the coefficients should be changed to minimize the error (i.e. move in the direction of the negative gradient of the error). The LMS algorithm will cause the filter coefficients to converge to a solution that will minimize the noise in the desired signal.

It is also possible for the adaptive filter to be placed in the inside transducer signal path a shown by filter 312, FIG. 5B.

As in the fixed filter case, this filter would change the frequency spectrum of the desired signal and a second filter 313 which is the inverse of adaptive filter 312 is needed after the subtraction is performed by summer 314 to remove the effects of filter 312 on the desired signal spectrum. Because the response of filter 312 is time varying, it is not possible to predetermine the characteristics of filter 313. The side chain processing of filters 315 and 316 is required in order to continuously generate the response characteristics of filter 313 which must be the inverse of filter 312. Filter 315 is a copy of filter 312. Filter 316 is arranged in such a manner that it will adapt itself to form the inverse of filter 315. Filter 315 needs to be driven by a white noise signal which contains energy at all in-band frequencies so that a complete inverse can be formed. If, for example, the signal input to filter 315 had no energy in a certain frequency band, filter 316 would have no information about how filter 315 would act on information in that frequency range if it were present in the signal, so it could not form an inverse in that range. Filter 313 is then a copy of filter 316.

The realizability of this configuration under all conditions is not guaranteed. The inverse of filter A may be unstable under certain conditions. The inverse may also require a filter length that exceeds the length that is allotted. This incomplete inverse would then affect the spectrum of the desired signal. This alternative is also much more computationally intensive than the preferred embodiment.

A third embodiment where some filtering is performed in the inside transducer signal path and some filtering is performed in the outside transducer path, FIG. 5C, is also possible. An application of an adaptive noise canceler with this configuration is described in "Real Time Digital Signal Processing Applications with Motorola's DSP 56000 Family" by Mohamed El-Sharkawy, published by Prentice Hall. Note that this configuration will still suffer from the requirement to generate an inverse filter for filtering that is done in the inside transducers signal path. This configuration can be set up, however, to guarantee that an inverse is realizable (although its length may still exceed the available space).

Preferred and alternative embodiments of the muting circuit for the fixed cancellation filter implementations of the stethoscope of this invention are shown in FIGS. 6A and 6B, respectively. Circuit 52a, FIG. 6A, prevents excessive noise signals from being amplified by the system when the chest piece is removed from the patient's chest in a high noise environment. Muting circuitry 52a senses when this condition occurs and activates the mute function by opening analog switch 350 to prevent an extremely loud signal at the user's ears. High pass filter 340 looks for high frequency energy in the output of the subtractor. The filter signal is full wave rectified by RMS detector 342 and low pass filtered by filter 344, and the signal is compared to a preset threshold DC level from reference voltage generator 346. When the detected level exceeds the threshold, comparator 348 changes state and opens analog switch 350. The alternative embodiment includes a chest piece mounted mechanical microswitch 352, FIG. 6B, which opens analog switch 354 when the chest piece is removed from the patient's skin. The switching could be accomplished with a type of force sensing or proximity sensing device, or a mechanical switch.

FIGS. 7A and 7B detail two embodiments of a circuit for accomplishing the signal compression/limiting functions of FIGS. 2 and 3. FIG. 7A shows a feedback topology and FIG. 7B shows a feed forward topology. In each case, a variable gain amplifier 490, 490a is inserted into the signal path. The detector circuits 492 and 492a compare the level of the signal to some internally pre-set threshold. When the threshold is exceeded, the control processors 494 and 494a send a control signal to the variable gain amplifiers 490 and 490a that adjusts their gain appropriately. Time constants in the detector circuits determine how quickly the control processor reacts to changes in the signal amplitude. Other circuitry in the control processor determines how much gain reduction to apply to the variable gain amplifiers. The total amount of gain reduction depends on the setting of this control circuitry. Limiting typically refers to a compression ratio of 10:1 or greater. Compression typically refers to compression ratios less than 10:1. These circuits can be developed in analog form using devices such as the THAT Corporation model 2150A voltage controlled amplifier and model 2252 RMS level detector. Circuit diagrams are available from THAT Corporation in their standard product literature that detail the topology required for operation as a limiter and compressor. These two devices provide the basic blocks shown in FIGS. 7A and 7B.

There have been numerous algorithms published in the audio engineering literature describing methods for achieving signal limiting and compression using digital signal processing techniques that would be compatible with the digital system embodiment of FIG. 3A. One such algorithm is described in D. Mapes-Riordan and W. M. Leach, Jr., "The Design of a Digital Signal Peak Limiter for Audio Signal Processing", J. Audio Eng. Soc. Vol. 36, pages 562–574 (1988).

The third basic portion of the stethoscope of this invention as shown in FIG. 1A is the earphones. In high noise environments, the headset must provide a high degree of noise attenuation or the ambient noise levels will mask the desired signal. Noise attenuation may be accomplished passively, actively, or by using a combination of both technologies. Passive attenuation methods tend to be effective at higher frequencies. Active attenuation methods tend to be effective at low frequencies. This invention requires attenuation at both low and high frequencies to maximize performance. This can be achieved by using a headset that combines both passive and active attenuation methods.

Passive attenuation may be accomplished by using a sealed ear cup design with an air tight seal between the ear cup and the user's head. An ear cup with a flexible seal (rubber, silicone, etc. ) and high head clamping force is usually used. Increasing the head clamping force reduces the noise transmission through the ear cup, but at the expense of user comfort. It is also helpful if the ear cups are massive. Passive attenuation can also be accomplished by using an in the ear type ear piece which blocks the ear canal. However, significant attenuation at frequencies below a few hundred hertz is extremely difficult to achieve solely with passive means.

Active cancellation is required to achieve significant noise attenuation at low frequencies. One headphone embodiment shown in FIG. 8A shows an active open loop noise cancellation system. In this embodiment, the outside microphone 501 picks up the ambient noise signal. It does not hear much signal from the headphone speaker 508 through the sealed ear cup 506. The microphone can be omni-directional or it can use a directional pickup pattern (such as a cardioid, hyper cardioid, super cardioid, etc.). If a directional microphone were used, the microphone would be oriented so that the null in its pickup pattern was pointed at the ear cup. This orientation will significantly reduce the chances of feedback occurring. The signal from the microphone is amplified by amplifier 502 and passed through a fixed noise cancellation filter 503. The output of this filter is passed to the inverting input of summer 504. The desired signal is passed through volume control 505 and on to the non-inverting input of summer 504. The output of the summer is then sent to headset amplifier 507 which is connected to speaker 508 in the ear cup. A separate microphone and signal processing circuit is required for each ear cup. The outside microphone should be located as close to the ear cup as possible for maximum cancellation. Note that using a directional microphone may result in lower maximum possible cancellation than using an omni directional microphone.

Figure 8C:
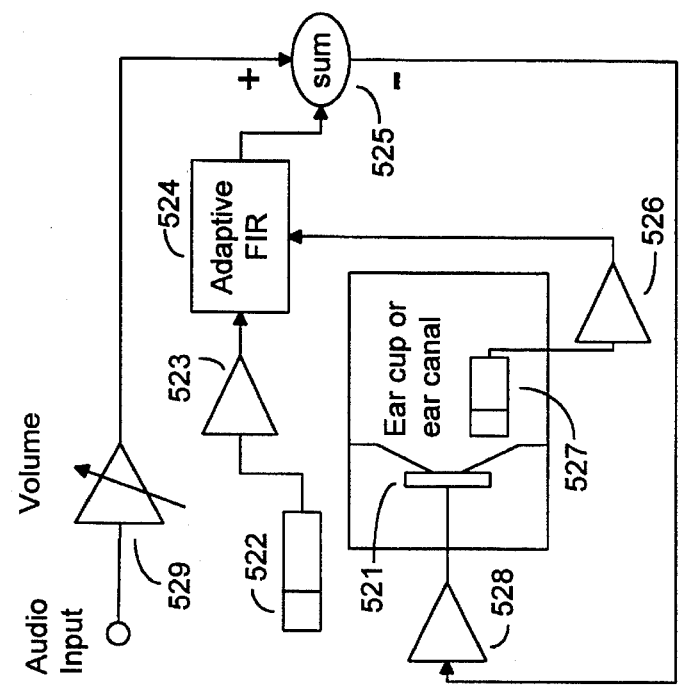
FIGS. 8A through 8C are schematic diagrams of three embodiments of the active noise cancellation headset for the noise reducing stethoscope of this invention.
Figure 8A:
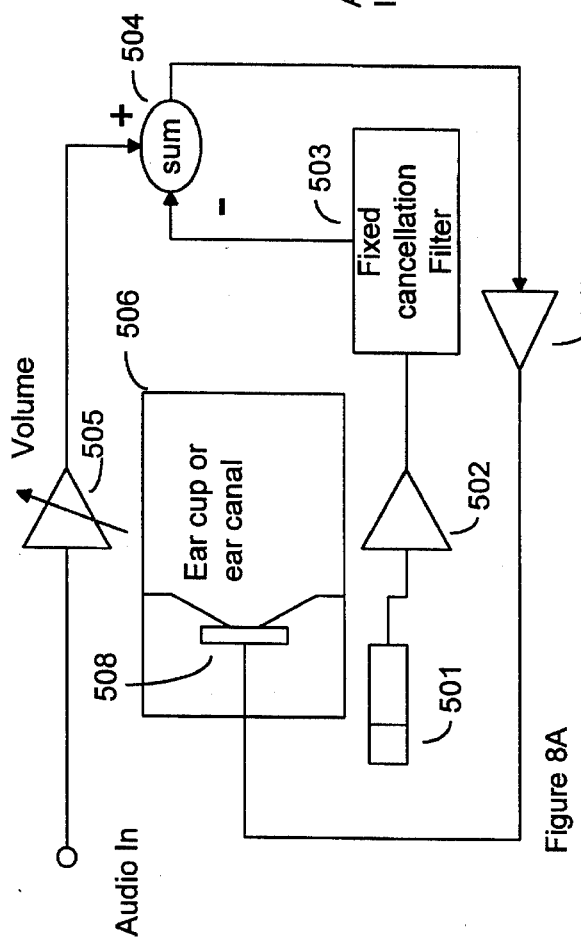
Figure 8B:
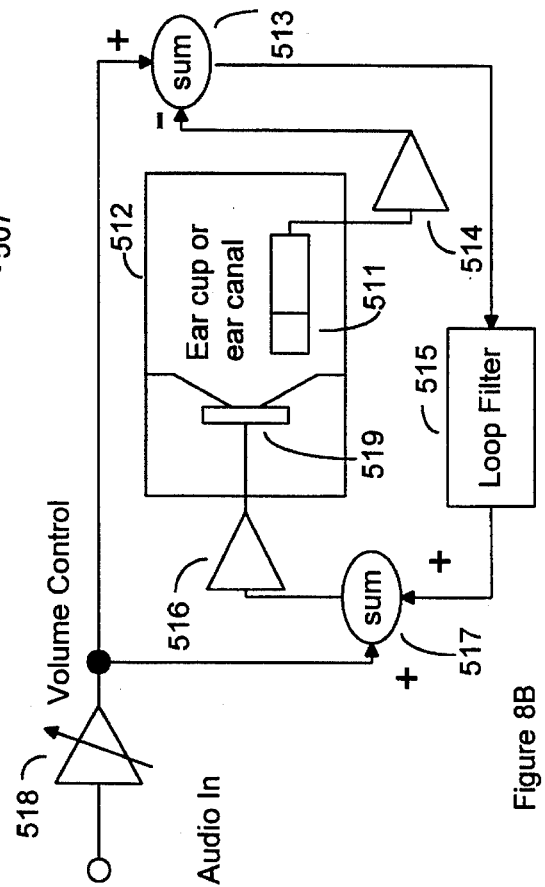

FIG. 8B shows a closed loop active noise cancellation topology embodiment. In this embodiment, the noise sensing microphone 511 is located inside the ear cup. Omni directional microphones are generally used here. The microphone will hear noise leakage through the ear cup as well as any signal generated by the speaker element. In this case, the output of microphone 511 is amplified by amplifier 514, and passed to the inverting input of summer 513. The desired signal is passed through volume control 518 and then to the non-inverting input of summer 513. The output of summer 513 then passes through loop filter 515. The loop filter is required to maintain stability of the feedback loop in this embodiment. The loop filter is designed to reduce the amplifier gain sufficiently to eliminate the possibility of feedback at any frequency where the phase shift through the loop approaches 180° (in addition to the signal inversion). If there is a frequency where the loop gain is greater than one and phase shift through the loop is 180° (360° with the inversion due to using negative feedback), then positive feedback will occur and the system will become unstable. The loop filter is designed to eliminate this. This filtering to maintain stability has the drawback of limiting the frequency range where cancellation occurs (unlike the open loop case). The output of the loop filter is then sent to the second summer 517. The desired signal is also input to this summer, just before the headphone amplifier. The desired signal is injected in two different places in the loop to keep from having the loop cancel the desired signal as well as the noise. The output of summer 517 is then fed to the headphone amplifier 516 and then to speaker 519.

FIG. 8C shows an adaptive active noise cancellation embodiment. In this embodiment, outside microphone 522 hears primarily noise. Its output is amplified by amplifier 523 and is then filtered by the adaptive filter 524. The output of the adaptive filter is connected to an inverting input of summer 525. The desired signal is connected to a volume control 529 which itself is connected to a non-inverting input of summer 525. The output of summer 525 then feeds amplifier 528 which drives speaker 521. Inside microphone 527 listens to the signal and noise inside the ear cup. This signal is amplified by amplifier 526 and sent to the control input of the adaptive filter 524. The inside microphone signal is used to control the response of adaptive filter 524. The topology is configured so that the filter response will adapt to minimize the power in the inside microphone signal. This occurs when noise cancellation is a maximum. This system does not suffer from the potential instabilities of the closed loop system. It can operate over a larger frequency range. Its effectiveness will reduce at frequencies where the sound pressure inside the ear cup varies as a function of position within the ear cup. When this occurs, cancellation at the microphone location may not imply that there is cancellation at the user's eardrum. This effect determines the high frequency limit for active cancellation in this configuration. This effect also contributes to determining the high frequency limit for cancellation in the embodiment of FIG. 8B.

The closed loop and adaptive systems can compensate for changes in component values over time and different use conditions. The open loop system will tend to change over time and may need periodic adjustment. The open loop system is the lowest cost option and the easiest to develop, however.

Each of these embodiments can be used with an ear type of headset as well. This type of headset uses a small speaker that is coupled, either directly or through some type of adapter housing, to the user's ear canal. This arrangement also seals off the ear canal from the outside environment. The inside microphone would then be in the cavity between the transducer and the ear canal or in the ear canal directly. The outside transducer would be outside the speaker.

Active cancellation is also possible using open air type headsets. These headsets will not have significant passive attenuation but will be effective in the frequency range where active cancellation is occurring. The open loop and adaptive systems may be more susceptible to instability with this type headset.

The headset system shown in FIG. 8C can also be used in another way. FIG. 8C shows a diagram of one ear cup of a noise cancelling headset. Microphone 522 is mounted outside the ear cup and is exposed to ambient noise. There is analogous circuitry not shown for the second ear cup of the headset. Microphone 522 and its counterpart on the other ear cup may used to perform the same function as the ambient noise sensors 26a, 84a, 26b, 84b in FIGS. 2A and 3A. It also is possible to use a single microphone in place of these two microphones to detect ambient noise, as long as the noise at the single microphone location is correlated with the noise at each ear cup. Use of the headset noise sensor or sensors to generate an ambient noise signal to cancel noise in the body sound sensor signal would eliminate the need for a separate ambient noise sensing transducer in the chest piece. The viability of this configuration will depend on the correlation between the noise at the headset noise sensor or sensors and the noise at the chest piece. To the extent that the noise is correlated, the configuration shown in FIG. 8C, which is designed to cancel ambient noise that leaks through the ear cup, will also act to cancel noise components in the signal. This configuration would not need (although it could contain them if desired) the cancellation filters 44, 86, 156, 166 shown in FIGS. 2A and 3A. The output of amplifier 523 of FIG. 8C would feed the adaptive FIR filter 524 as shown as well as the associated FIR filter for the other ear cup not shown. It could also feed filter 44 and 86 in FIG. 2A or anti-alias filters 153 and 163 in FIG. 3A. The adaptive FIR filter 524 and its counter part used for the second ear cup will adjust their response to cancel any signal inside the ear cups that is correlated with the output of the noise sensor. The system does not distinguish between noise that leaks through the ear cup and noise that is pan of the body sound sensor signal as long as the noise to be cancelled is correlated with the noise sensor. It is this characteristic that would allow the possible elimination of the cancellation filters in FIGS. 2A and 3A discussed earlier.

As discussed above, a system can be developed where only one ambient noise sensor is used. The sensor could be located on the chest piece, on the headset, or somewhere in between. Locating the sensor in the chest piece would tend to maximize noise cancellation in the body sound transducer signal at the possible expense of cancellation of leakage noise through the headset. Locating the sensor at the headset would tend to favor cancellation of leakage noise over cancellation of noise in the body sound signal. The optimum arrangement, however, will still have one noise sensing transducer located as close as is physically possible to the body sound sensor to maximize the correlation between the ambient noise sensed and the noise that contaminates the signal, and will use the configuration shown in FIGS. 2 and 3 for cancellation. It will also use separate noise sensors located next to the ear cups of the headset in the configuration shown in FIG. 8C to maximize the correlation between the noise that leaks through the ear cup and the noise that is sensed so that cancellation of noise leakage will also be maximized.

Figure 9:
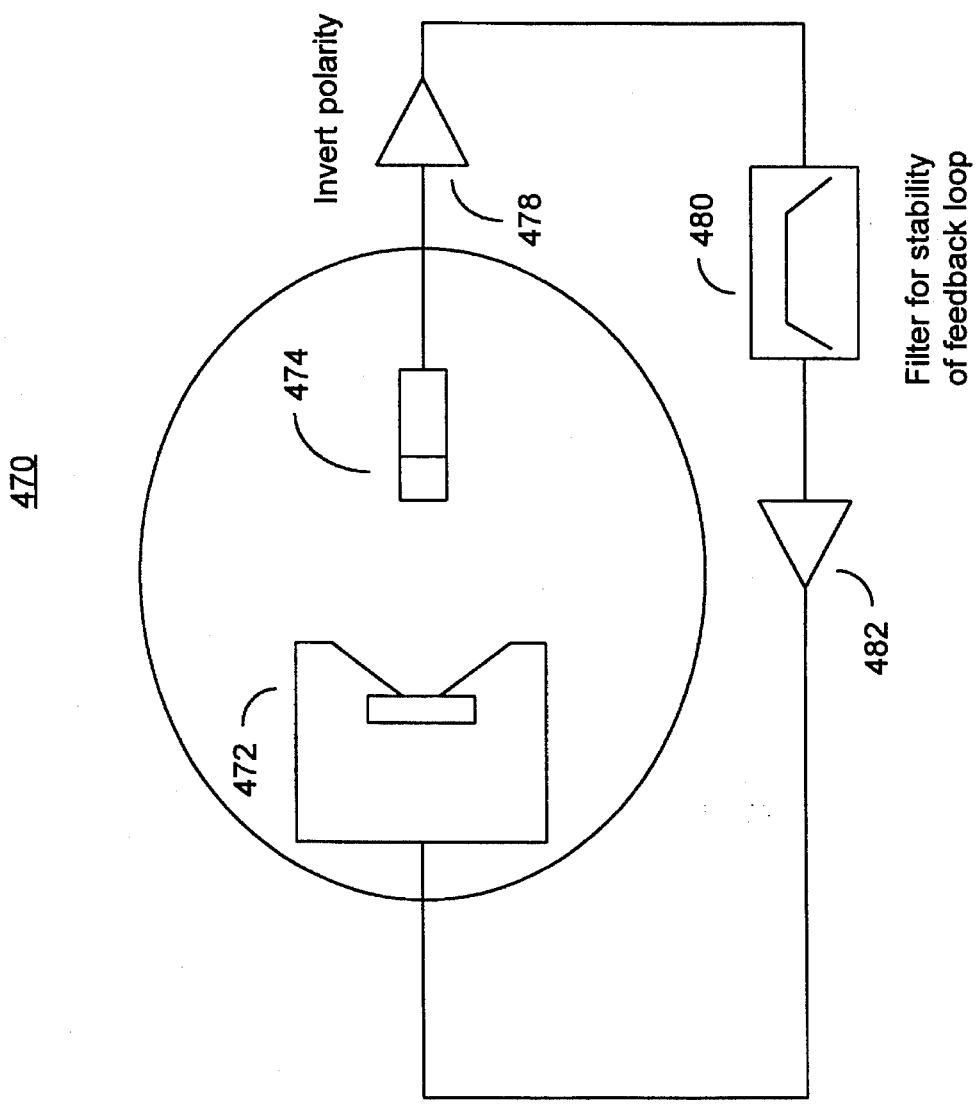
FIG. 9 is a schematic diagram of an alternative means of cancelling noise at the chest piece for the noise reducing stethoscope of this invention.

FIG. 9 details another method of cancelling noise at the chest piece. System 470 includes noise cancelling speaker 472, sensing microphone 474, polarity inverting microphone pre-amplifier 478, loop filter 480, and amplifier 482. Noise is heard by microphone 474, amplified and inverted by pre-amplifier 478, filtered by loop filter 480, amplified by amplifier 482 and fed to noise canceling speaker 472. This feedback loop acts to maintain zero pressure at the microphone by playing back the transduced noise signal with reversed polarity so it will cancel the ambient noise. In effect, a zone where cancellation is occurring is created around the speaker and microphone, indicated by the oval. The size of the zone varies as a function of frequency and depends on the relative positions of the microphone and speaker. In this embodiment, the chest piece would be located within this zone. This concept can be used with any standard acoustical stethoscope, or any amplified stethoscope including any of the embodiments of this invention as described above with any of the described headset configurations. This "zone of silence" concept was first described by H. F. Olsen and E. G. May in "Electronic Sound Absorber", Journal of the Acoustical Society of America 25, pages 1130–1136, 1953. The system above cancels noise acoustically rather than electrically as described in the preferred embodiment of this invention.

Four alternative transducer designs for the stethoscope of this invention are shown in FIGS. 10A through 10D. These designs employ a single transducer and also accomplish noise cancellation; the noise cancellation is accomplished directly by the transducer itself. Transducers that accomplish this noise cancellation are typically referred to as noise canceling microphones and are available from many manufacturers, the Primo model EM124 being an example of an electret condenser type noise canceling microphone. These microphones have what is known as a first order gradient or a pressure gradient response characteristic; they produce an electrical output which is proportional to the pressure difference between the two sides of the diaphragm. Use of this type of transducer is compatible with all existing chest piece types.

The noise cancellation provided by these types of microphones is accomplished by exposing the front of the diaphragm to the desired signal (along with noise that leaks through the body seal), and the rear of the diaphragm only to the noise source. Transducer 540, FIG. 10A, is mounted in the chest piece bell 541 so that the front of the diaphragm is inside the bell and the rear of the diaphragm is exposed to the outside environment. A typical microphone used would be an electret condenser type where the hole in the back of the capsule exposes the rear of the diaphragm to the outside environment. Noise that leaks through the chest piece will affect the front of the diaphragm. That same noise will also reach the rear of the diaphragm through the hole in the capsule housing. There is an inherent 180° phase shift between sound at the front and rear of the diaphragm. If the pressures due to external noise are equal on both sides of the diaphragm, the diaphragm will not move and the microphone will not generate an electrical signal. This arrangement can also be used in a diaphragm-type chest piece, FIG. 10B.

Figure 10C:
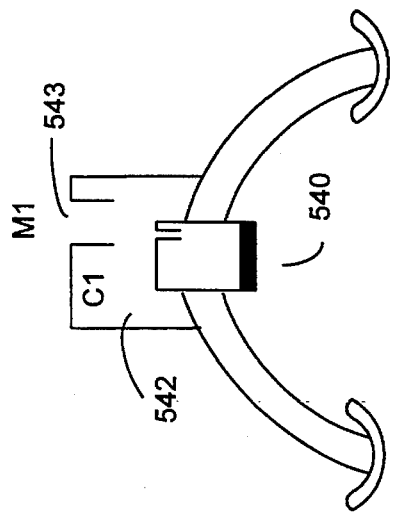
FIGS. 10A through 10D are schematic cross-sectional diagrams of four alternative noise cancelling sound transducer designs for the noise reducing stethoscope of this invention.
Figure 10D:
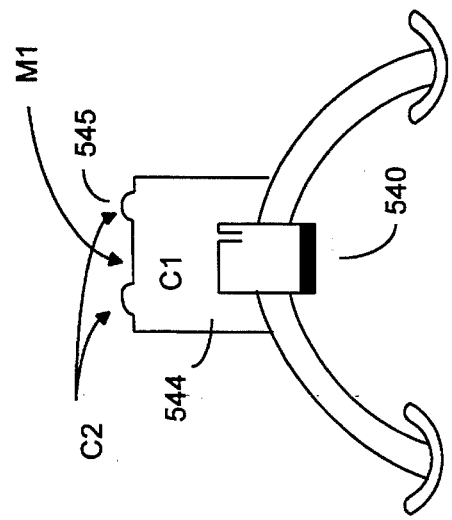
Figure 10A:
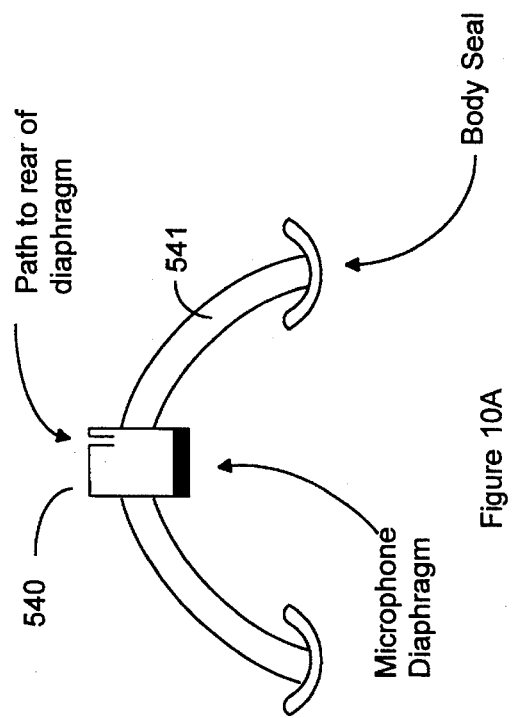
Figure 10B:
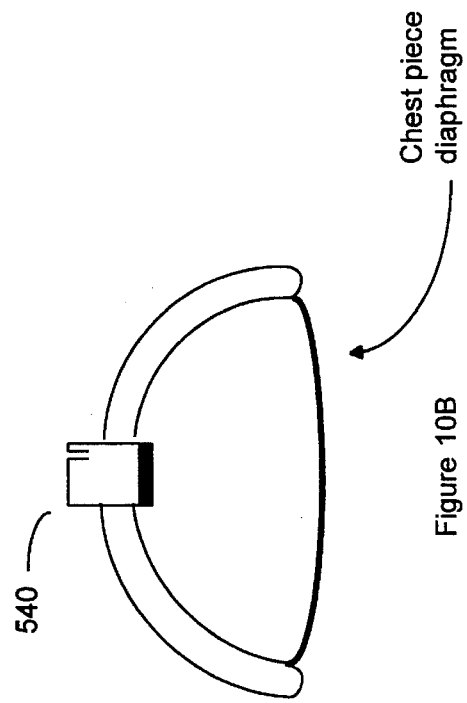

In order to extend the frequency range over which cancellation occurs, housing 542, FIG. 10C, around the rear of the microphone 540 needs to be constructed so that the transfer function from an ambient noise source to the from of the diaphragm is exactly the same as the transfer function from that same ambient source to the rear of the diaphragm (except for the inherent 180° phase difference which is desired). This can be done by designing the housing to have certain geometrical features that act like acoustical filter elements. These acoustical elements can be designed directly into the microphone capsule housing or can be included in the chest piece housing. In the example system described earlier, a second order low pass filter at 700 Hz was required to match the transfer function of the outside transducer to that of the inside transducer. This type of filter can be constructed using an acoustical compliance C1 and an acoustical mass M1 as filter elements. The values of the mass and compliance are chosen to resonate at a particular frequency (700 Hz in the example but it will depend on the exact chest piece configuration used). Below that frequency, noise will be transmitted directly to the rear of the microphone diaphragm. Above the resonant frequency, the sound that reaches the rear of the diaphragm will roll off at 12 dB per octave (second order) due to the effects of the acoustical mass and compliance (6 dB per octave for each filter element). It is also possible to construct a rear chamber 544, FIG. 10D, that is covered with a diaphragm 545 to perform the filtering. Diaphragm 545 also has the advantage of closing off outside access to microphone 540, which will prevent buildup of contaminants in the microphone. The diaphragm will be chosen to have a particular mass M1. It will also have a mechanical compliance C2. The enclosed volume between this second diaphragm and the rear side of the microphone diaphragm is another compliance that acts in concert with the compliance of the diaphragm. The volume of this rear chamber and the compliance of the second diaphragm are chosen so that the total compliance resonates with the second diaphragm mechanical mass at the desired frequency. The diaphragm has mechanical mass which acts in an analogous fashion to the acoustical mass described above.

Other types of transducers besides electret condenser microphones can also be used to accomplish this cancellation. The essential features are that there be a diaphragm that separates the bell from the outside environment as shown, that the front of the diaphragm is exposed to signal plus ambient noise and the rear of the diaphragm is exposed only to the noise, the motion of the diaphragm is converted to an electrical signal by some transduction method, and that the construction of the housing is designed so that the pressures on each side of the diaphragm due to an ambient noise source are as equal as possible.

Figure 11:
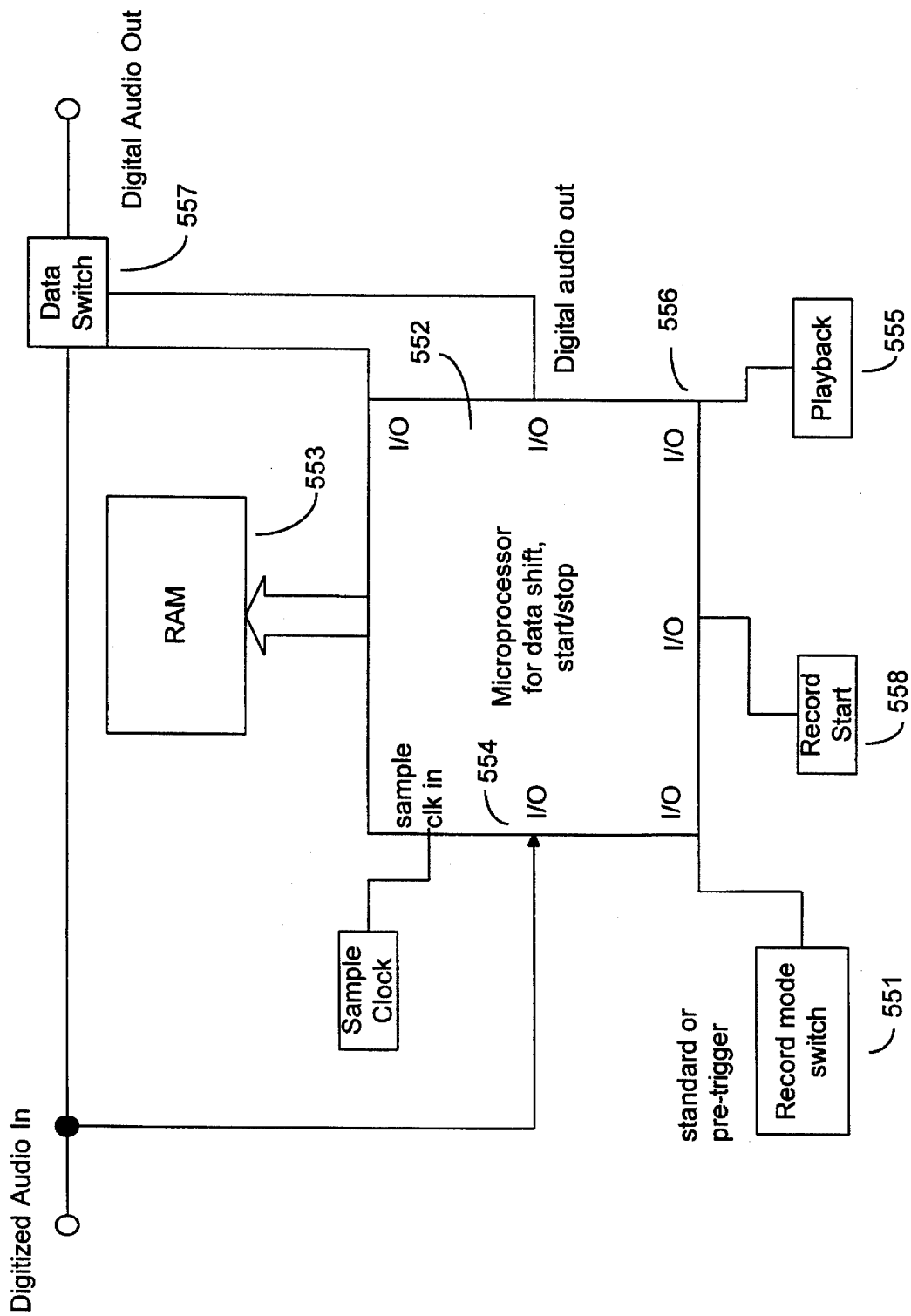
FIG. 11 is a schematic diagram of a digital recording system for the noise reducing stethoscope of this invention.

FIG. 11 is a digital embodiment of a system for providing an electronic recording capability for body sounds. This would be used if some anomalous sound were heard and the physician wanted to listen to it again. This recording system could be set up to operate in two different modes—normal, or pre-trigger mode—chosen with switch 551. Normal mode would capture data starting with the activation of record switch 558. Pre-trigger operation is designed to capture a portion of the signal prior to the time the record switch is activated. This is very useful for capturing events that only occur intermittently. The pre-trigger removes the delay of human reaction time and makes it easy to capture one-time events. This pre-trigger function is commonly used in digital storage oscilloscopes for capturing one-time events. It should be understood that the algorithms described below are not the only ones that could be used to accomplish the recording and pre-trigger functions described.

For normal recording, the memory address register of the microprocessor would be initialized to address 1. The microprocessor 552 would be idle until record switch 558 is activated by the user. After the switch is activated, the processor will read in a data value from I/O port 554 and write that data sample into RAM 553 each sample clock cycle. The processor would write the first data sample to RAM 553 at the memory location specified in the memory address register and then increment the memory address register by one. The next sample clock cycle, another data sample would be read in and written to the second memory location and the memory address register would be incremented again. This process would continue until the last memory location was written. Then the processor would return to an idle state. Using a 6 KHz sample rate with a 16 bit data word (2 bytes), 30 seconds of storage would require a memory buffer that could hold 180,000 data words. This would need a minimum of 360 Kbytes of RAM. A larger amount of RAM can be used if longer recording is needed. This is a straight forward digital recording function of which there are numerous examples in the digital audio signal processing field. The preferred embodiment of this system has this processing done in a side chain so that normal operation is not affected while recording is in process. Playback of the recorded signal is discussed below.

Operation in pre-trigger mode requires a slightly different processing mode. The system would be set up to record as in the normal record mode, but it would record continuously. When the processor writes the last data location in RAM, the address pointer would cycle back to the first memory location in RAM and continue the process, overwriting the previously stored data. This generates a circular RAM buffer. When the record switch is activated, a counter would be initialized to zero. Data continues to be written to RAM as described. The counter is incremented by one each time a data sample is written to RAM. Recording will continue until the counter reaches a preset number. The number is determined by the total number of memory locations available and the length of pre trigger time desired. Using the previous example where thirty seconds of storage is available, assume that ten seconds of pre trigger is desired. Thirty seconds of storage requires 180,000 16 bit memory locations. Ten seconds of pre trigger requires 60,000 16 bit memory locations. The maximum counter value should then be set to 180,000−60,000=120,000. When the counter reaches 120,000, recording would stop and the microprocessor address pointer will be incremented so that it is pointing to the correct memory location for playback to begin.

A playback button 555 connected to another I/O port 556 could be activated to play back the contents of the RAM buffer. Playback for recordings made under normal trigger conditions would begin at memory location one and proceed to the end of the buffer. Playback for recordings made under pre-trigger conditions would begin at the memory address pointed to by the microprocessor address register. Playback would continue until 179,999 memory locations have been read out, and then stopped. This would be one cycle through memory. This sequence would be repeated each time the playback button is pressed. A continuous playback function could also easily be provided. The playback control would activate switch 557 which controls whether the output of the RAM buffer is passed to the rest of the system or whether digital data passes straight through the system bypassing the storage system. When normal functioning is desired, the record button 558 can be pressed again to reset the system and change switch 557 back to bypass mode. It is also possible to achieve these functions with an analog system.

Although specific features of the invention are shown in some drawings and not others, this is for convenience only as some feature may be combined with any or all of the other features in accordance with the invention.

Other embodiments will occur to those skilled in the art and are within the following claims:

What is claimed is:

1. A noise-reducing stethoscope for sensing body sounds in the presence of ambient noise external to the body, comprising:
   a body sound sensor adapted for coupling to a body to detect primarily the internal body sounds and output in response a body sound electrical signal having a first signal to noise ratio;
   an ambient noise sensor, disposed to detect primarily the ambient noise external to the body and output in response an ambient noise electrical signal; and
   means for processing said body sound electrical signal and said ambient noise electrical signal to create a third signal having a greater signal to noise ratio than that of said body sound electrical signal.

2. The noise-reducing stethoscope of claim 1 in which said body sound sensor is a microphone.

3. The noise-reducing stethoscope of claim 1 in which said ambient noise sensor is a microphone.

4. The noise-reducing stethoscope of claim 1 further including means for filtering said ambient noise electrical signal to make said ambient noise electrical signal contribution from ambient noise closer to said body sound electrical signal contribution from ambient noise, to achieve better noise cancellation in said third signal.

5. The noise-reducing stethoscope of claim 4 in which said means for filtering said ambient noise electrical signal includes a time invariant filter.

6. The noise-reducing stethoscope of claim 4 in which said means for filtering said ambient noise electrical signal includes a time variant filter that continuously adapts its frequency response to maximize noise cancellation.

7. The noise-reducing stethoscope of claim 1 further including a single stethoscope chest piece adapted for placement on a body, and on which at least one of said sensors is mounted.

8. The noise-reducing stethoscope of claim 7 wherein said chest piece has a cavity, adapted for coupling to the body, that acts as an acoustic compliance, and in which said body sound sensor is mounted on said stethoscope chest piece so that it is coupled to said cavity of said stethoscope chest piece.

9. The noise-reducing stethoscope of claim 7 in which said ambient noise sensor to said stethoscope directly senses sound outside of said chestpiece.

10. The noise-reducing stethoscope of claim 1 wherein said third signal has a level as a function of frequency, the stethoscope further including low pass filter means for filtering said third signal to reduce said third signal level above a predetermined frequency.

11. The noise-reducing stethoscope of claim 10 in which said means for filtering said third signal includes a time invariant filter.

12. The noise-reducing stethoscope of claim 1 further including means for filtering said body sound electrical signal to make the portion of said body sound electrical signal due to ambient noise more closely match the portion of said ambient noise electrical signal due to ambient noise.

13. The noise-reducing stethoscope of claim 12 wherein said means for filtering said body sound electrical signal has a first transfer function with a magnitude response as a function of frequency and a phase response as a function of frequency, and further including means for filtering said third signal, in which said means for filtering said third signal has a second transfer function whose magnitude response over a frequency range is an inverse of the magnitude response of said first transfer function of said means for filtering said body sound electrical signal.

14. The noise-reducing stethoscope of claim 12 in which said means for filtering said body sound electrical signal includes a time invariant filter.

15. The noise-reducing stethoscope of claim 12 in which said means for filtering said body sound electrical signal includes a time variant filter that continuously adapts a frequency response to maximize noise cancellation.

16. The noise-reducing stethoscope of claim 1 wherein the stethoscope has a gain and said third signal has a level, and further includes dynamic variable gain means for adjusting said gain as a function of the level of said third signal.

17. The noise-reducing stethoscope of claim 16 in which said variable gain means includes a variable gain amplifier.

18. The noise-reducing stethoscope of claim 16 in which said variable gain means includes gain reduction control means for outputting a control signal to said variable gain amplifier to change said gain as determined by said gain reduction control means.

19. The noise-reducing stethoscope of claim 16 wherein said third signal has a maximum level, wherein said variable gain means includes means for limiting the maximum level of said third signal to eliminate clipping distortion.

20. The noise-reducing stethoscope of claim 16 wherein said third signal has a dynamic range and a perceived loudness, in which said variable gain means includes means for compressing the dynamic range of said third signal to increase the perceived loudness of said third signal.

21. The noise-reducing stethoscope of claim 16 wherein said gain changes at a speed, and in which said variable gain means includes signal processing means for controlling the speed at which said gain changes as a function of the level of said third signal, said signal processing means including attack means for controlling the speed of gain reduction, and decay means for controlling the speed at which gain is returned to its original value.

22. The noise-reducing stethoscope of claim 16 wherein said gain changes at a speed, and in which said variable gain means includes signal processing means for controlling the speed at which said gain changes as a function of the level of said third signal, said signal processing means including attack means for controlling the speed of gain reduction when a set threshold is exceeded, and decay means for controlling the speed at which gain is returned to its original value after the input signal has dropped below the threshold.

23. The noise-reducing stethoscope of claim 1 further including means for muting said third signal in noisy environments when the chest piece is not against the body.

24. The noise-reducing stethoscope of claim 1 further including high pass filter means with a variable cut-off frequency for filtering low frequency cardiac sounds to make higher frequency sounds more audible.

25. The noise-reducing stethoscope of claim 1 in which said means for processing said body sound electrical signal and said ambient noise electrical signal includes means for subtracting said ambient noise electrical signal from said body sound electrical signal to create a difference signal with decreased noise artifacts as compared to said body sound electrical signal.

26. The noise-reducing stethoscope of claim 1 further including a headset for playing said third signal.

27. The noise-reducing stethoscope of claim 26 in which said headset includes means for attenuating the ambient noise.

28. The noise-reducing stethoscope of claim 26 further including means for accepting a radio input to allow said radio input to be played in said headset.

29. The noise-reducing stethoscope of claim 27 in which said means for attenuating the ambient noise includes means for passively attenuating noise.

30. The noise-reducing stethoscope of claim 29 in which said means for attenuating the ambient noise includes a sealed ear cup headset.

31. The noise-reducing stethoscope of claim 30 wherein said headset includes ear cups with flexible seals, and in which said means for attenuating the ambient noise further includes means for providing high head clamping force between the ear cups and the user's head.

32. The noise-reducing stethoscope of claim 27 in which said means for attenuating ambient noise includes a headset that is adapted to fit into a user's ear canal and provides a seal that blocks the ear canal to increase passive noise attenuation.

33. The noise-reducing stethoscope of claim 27 in which said means for attenuating the ambient noise includes means for actively attenuating the ambient noise.

34. The noise-reducing stethoscope of claim 33 in which said means for actively attenuating the ambient noise includes a sensing microphone for sensing the ambient noise, and a speaker element, responsive to the microphone, for playing sound to cancel the sensed ambient noise.

35. The noise-reducing stethoscope of claim 27 in which said means for attenuating the ambient noise includes both passive and active noise attenuation means for both passively and actively attenuating the ambient noise.

36. The noise-reducing stethoscope of claim 1 further including means for creating and broadcasting a radio output from said third signal.

37. The noise-reducing stethoscope of claim 1 further including a speaker, responsive to said third signal, for playing said third signal to allow simultaneous monitoring by a large number of people.

38. The noise-reducing stethoscope of claim 1 further including a stethoscope chest piece, in which at least said body sound sensor is in said stethoscope chest piece, and further including an electrical connector on said chest piece.

39. The noise-reducing stethoscope of claim 38 further including a sensor operatively connected to said electrical connector for sensing the presence of a chest piece.

40. The noise-reducing stethoscope of claim 38 further including a signal amplifier in said chest piece.

41. The noise-reducing stethoscope of claim 1 wherein said third signal has subsonic elements, the stethoscope further including a subsonic filter, responsive to said third signal, for filtering subsonic elements from said third signal.

42. The noise-reducing stethoscope of claim 1 further including a memory buffer, responsive to said third signal, for capturing a short length time segment of said third signal for immediate playback and review.

43. The noise-reducing stethoscope of claim 42 further including user-operable record means, responsive to said third signal, for enabling said memory buffer to record said third signal.

44. The noise-reducing stethoscope of claim 43 in which said memory buffer includes means for capturing said third signal before enablement of said memory buffer by said record means, to allow capture of events happening before user operation of said record means.

45. The noise-reducing stethoscope of claim 1 wherein said third signal has a spectrum and a level, the stethoscope further including loudness compensation means for modifying the spectrum of said third signal as a function of said third signal level.

46. The noise-reducing stethoscope of claim 45 in which said loudness compensation means includes a dynamic filter into which said third signal is input, and which has a frequency response which varies as a function of level, wherein the frequency response of said dynamic filter alters the level of low frequency signal with respect to the level at mid and high frequencies, and wherein said low frequency signal level increases less than the increases of the mid and high frequency signal levels when the third signal level is increased, and wherein the low frequency signal level decreases less than the decrease of said mid and high frequency levels when said third signal level is decreased.

47. The noise-reducing stethoscope of claim 1 further including transducer means for converting a user's speech into an electrical speech signal.

48. The noise-reducing stethoscope of claim 47 further including means for creating and broadcasting a radio output from said electrical speech signal.

49. A noise-reducing stethoscope, comprising:

a stethoscope chest piece including a first transducer adapted for placement on a body to detect primarily internal body sounds and output in response a first electrical signal with a contribution from ambient noise external to the body, and a second transducer, proximate the first, to detect primarily the ambient noise and output in response a second electrical signal;

means for combining said first and second electrical signals to create a combined signal with a contribution from the ambient noise which is less than the contribution from the ambient noise to said first electrical signal; and a noise-attenuating headset, responsive to said combined signal, and including earphones for playing said combined signal.

* * * * *